United States Patent [19]
Johnston et al.

[11] Patent Number: 5,989,553
[45] Date of Patent: Nov. 23, 1999

[54] EXPRESSION LIBRARY IMMUNIZATION

[75] Inventors: Stephen A. Johnston, Dallas; Michael A. Barry, Carrollton; Wayne C. Lai, Richardson, all of Tex.

[73] Assignee: Board of Regents, The University of Texas System, Austin, Tex.

[21] Appl. No.: 09/001,157

[22] Filed: Dec. 30, 1997

Related U.S. Application Data

[62] Division of application No. 08/421,155, Apr. 7, 1995, Pat. No. 5,703,057.

[51] Int. Cl.$^6$ .......................... A61K 39/00; A61K 39/21
[52] U.S. Cl. .................................... 424/190.1; 424/184.1; 424/185.1; 424/188.1; 424/201.1; 424/207.1; 424/208.1; 424/234.1; 424/263.1; 424/264.1; 424/248.1; 435/325; 435/440; 435/455; 435/489; 530/403; 530/806; 530/825; 530/826; 530/868; 514/2
[58] Field of Search .............................. 424/184.1, 185.1, 424/188.1, 190.1, 201.1, 207.1, 208.1, 234.1, 263.1, 264.1, 248.1; 435/325, 440, 455, 489; 530/403, 806, 825, 826, 868; 514/2

[56] References Cited

U.S. PATENT DOCUMENTS

| | | | |
|---|---|---|---|
| 5,451,399 | 9/1995 | Gimbrone, Jr. et al. | 424/85.2 |
| 5,589,466 | 12/1996 | Feigner et al. | |
| 5,703,057 | 12/1997 | Johnston et al. | 514/44 |

FOREIGN PATENT DOCUMENTS

WO95/05853 3/1995 WIPO.

OTHER PUBLICATIONS

Davis et al., "DNA-based immunization induces continuous secretion of hepatitis B surface antigen and high levels of circulating antibody," *Human Molecular Genetics*, 2:(11)1847–1851, 1993.
Eisenbraun et al., "Examination of Parameters Affecting the Elicitation of Humoral Immune Responses by Particle Bombardment-Mediated Genetic Immunization," *DNA Cell Biol.* 12(9):791–797, 1993.
Fynan et al., "DNA vaccines: Protective Immunizations by parenteral, mucosal and gene-gun inoculations," *Proc. Natl. Acad. Sci. USA*, 90:11478–11482, 1993.
Kovacsovics-Bankowskiet al., "Efficient major histocompatibility complex class I presentation of exogenous antigen upon phagocytosis by macrophages," *Proc. Natl. Acad. Sci. USA*, 90:4942–4946, 1993.
Lai et al., "Protection of mice against experimental murine mycoplasmosis by a *Mycoplasma pulmonis* immunogen in lysogenized *Escherichia coli,*" *Vaccine*, 12(4):291–298, 1994.
Lowrie et al., "Towards a DNA vaccine against tuberculosis," *Vaccine*, 12(16):1537–1540, 1994.
Tang et al., "Genetic immunization is a simple method for eliciting an immune response," *Nature*, 356:152–154, 1992.
Ulmer et al., "Heterologous Protection Against Influenza by Injection of DNA Encoding a Viral Protein," *Science*, 259:1745–1749, 1993.

Wang et al., "Gene inoculation generates immune responses against human immunodeficiency virus type 1," *Proc. Natl. Acad. Sci. USA*, 90:4156–4160, 1993.
Xiang et al., "Vaccination with a Plasmid Vector Carrying the Rabies Virus Glycoprotein Gene Induces Protective Immunity against Rabies Virus," *Virology*, 199:132–140, 1994.
Klein, In: *Immunology: The Science of Self-Nonself Discrimination*, John Wiley & Sons, New York, pp. 6–9, 660–661, 1982.
Stryer, In: *Biochemistry*, W.H. Freeman and Co., San Francisco, p 732, 1975.
Soukhanov et al. (Eds.), In: *Webster's II. New Riverside University Dictionary*, The Houghton Mifflin Co., Boston, MA, p 67, 1984.
Ada, "Strategies for Exploiting the Immune System in the Design of Vaccines," *Molec. Immunol.*, 28(3):225–230, 1991.
Ausebel, Ed., In: Short Protocols in Molecular Biology *A Compendium of Methods from Current Protocols in Molecular Biology*, 2nd Ed., Harvard Medical School, publication date unknown.
Barry et al., "Production of Monoclonal Antibodies by Genetic Immunization," *BioTechniques*, 16(4):616–620, 1994.
Coney et al., "Facilitated DNA inoculation induces anti-HIV-1 immunity in vivo," *Vaccine*, 12(16):1545–1550, 1994.
Conry et al., "Immune Response to a Carcinoembryonic Antigen Polynucleotide Vaccine," *Cancer Research*, 54:1164–1168, 1994.
Cox et al., "Bovine Herpesvirus 1: Immune Responses in Mice and Cattle Injected with Plasmid DNA," *J. Virol.*, 67(9):5664–5667, 1993.
Barry et al., "Protection against mycoplasm infection using expression-library immunization," *Nature*, 377:632–635, 1995.
Crystal, "Transfer of genes to humans: Early lessons and obstacles to success," *Science*, 270:404–409, 1995.
Wang et al., "DNA inoculation induces cross clade anit-HIV-1 responses," *Annals of the New York Academy of Sciences*, 772:186–197, 1995.
Warner et al., "Retroviral vectors for HIV immunotherapy," *Annals of the New York Academy of Sciences*, 772:105–116, 1995.
Asubel et al., In: *Current Protocols in Molecular Biology*, John-Wiley & Sons, New York, pp. 6.0.3–6.0.4, 1988.

*Primary Examiner*—Laurie Scheiner
*Attorney, Agent, or Firm*—Arnold White & Durkee

[57] ABSTRACT

A general method for vaccinating against any pathogen is presented. The method utilizes expression library immunization, where an animal is inoculated with an expression library constructed from fragmented genomic DNA of the pathogen. All potential epitopes of the pathogen's proteins are encoded in its DNA, and genetic immunization is used to directly introduce one or more expression library clones to the immune system, producing an immune response to the encoded protein. Inoculation of expression libraries representing portions of the *Mycoplasma pulmonis* genome was shown to protect mice from subsequent challenge by this natural pathogen. Protection against Listeria.

6 Claims, 11 Drawing Sheets

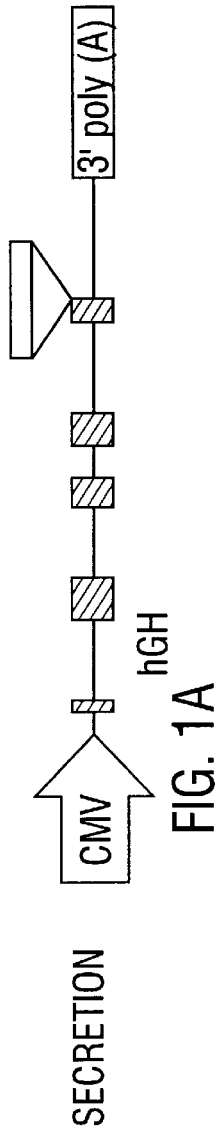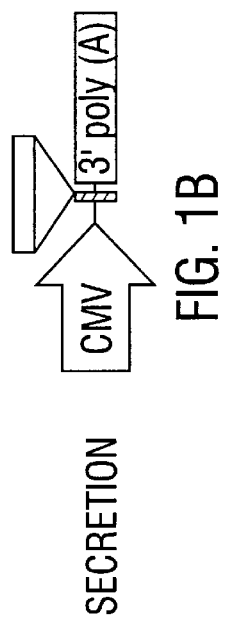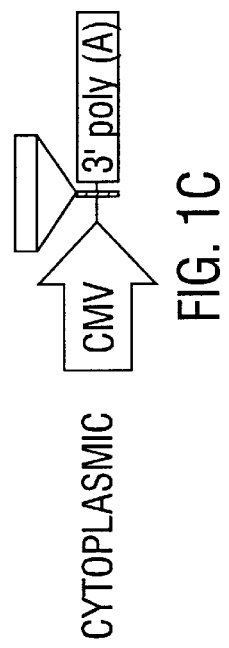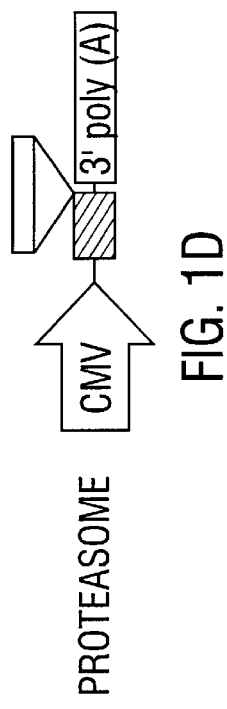

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:1:

GATCTTGGAT CCTAAGTAAG TA      22

(2) INFORMATION FOR SEQ ID NO:2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:2:

AGCTTACTTA CTTAGGATCC AA      22

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:3:

GATCGGATCC TAAGTAAGTA      20

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:4:

AGCTTACTTA CTTAGGATCC      20

(2) INFORMATION FOR SEQ ID NO:5:

(i) SEQUENCE CHARACTERISTICS:
      (A) LENGTH: 32 base pairs

```
            (B) TYPE: nucleic acid
            (C) STRANDEDNESS: single
            (D) TOPOLOGY: linear (xi) SEQUENCE DESCRIPTION: SEQ ID NO:5:

ACTGGGCAGA TCTTGGATCC TAAGTAAGTA AG                                    32

(2) INFORMATION FOR SEQ ID NO:6:

(i) SEQUENCE CHARACTERISTICS:
            (A) LENGTH: 8 amino acids
            (B) TYPE: amino acid
            (C) STRANDEDNESS:
            (D) TOPOLOGY: linear (xi) SEQUENCE DESCRIPTION: SEQ ID NO:6:

Thr Gly Gln Ile Leu Asp Pro Lys
1               5

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:7:

ACTGGGCAGA TCGGATCCTA AGTAAGTAAG                                       30

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:8:

Thr Gly Gln Ile Leu Asp
1               5
```

EXPRESSION LIBRARY IMMUNIZATION

The application is a divisional of patent application Ser. No. 08/421,155 filed Apr. 7, 1995 now issued as U.S. Pat. No. 5,703,057.

BACKGROUND OF THE INVENTION

1. Field of the Invention

The invention relates generally to methods for screening and obtaining vaccines generated from administration of expression libraries constructed from a pathogen genome. The method further includes identification of one or more antigenic plasmids that will elicit an immune response that is protective against pathogen challenge subsequent to inducing an in vivo immunogenic response. Also included in the invention are particular vaccine compositions protective against Listeria and Mycoplasma.

2. Description of Related Art

While vaccination is one of the most cost-effective medical methods for saving lives, vaccines have not been developed for many of the most serious human diseases, including respiratory syncytial virus (RSV), pneumonia caused by *Streptococcus pneumoniae*, and diarrhea caused by rotavirus and Shigella. As is evident with the HIV epidemic, the increase in tuberculosis and the endemic spread of malaria and other parasitic diseases, there is an increasing need to develop effective vaccines, yet for many of these pathogens daunting scientific problems have arisen. For example, the influenza virus is notorious for antigenic drift so that new vaccines are constantly being developed; research efforts continue in attempts to identify effective vaccines for rabies (Xiang, et al, 1994), herpes (Rouse, 1995); tuberculosis (Lowrie, et al, 1994); HIV (Coney, et al, 1994) as well as many other diseases of importance in developed and undeveloped countries. Yet there exists no relatively rapid, yet alone systematic, means of identifying an effective vaccine, much less a reasonable assurance that, once identified, the vaccine will be broadly responsive to pathogen challenge.

Many currently used vaccines are composed of live/attenuated pathogens (Ada, 1991) which when inoculated infect cells and elicit a broad immune response in the host. While highly detailed knowledge of the pathobiology is not necessary, at the very least isolation and identification of the pathogen is required. Live vaccines are often superior to antigen or subunit vaccines because of their tendency to elicit a broad level protective response; however, serious disadvantages in using such vaccines include the risk of a vaccine-induced infection, problems with producing and storing the vaccine, and failure to engender any immune response; for example, where antigen presentation is limited. Perhaps the most troubling aspect of using live vaccines is the propensity for actually causing the disease against which protection is intended. Past experience with some of the polio and measles vaccines has demonstrated that this may be a serious risk.

An alternative to the use of live/attenuated pathogen vaccines is to use antibodies to single proteins or to a limited number of proteins associated only with the pathogen. Polyclonal or monoclonal antibodies are readily produced with the aid of modern hybridoma technology, although these techniques are relatively expensive and time consuming. There is also no assurance that antibodies produced in response to an antigen will provide protection against the pathogen providing the antigen; consequently, it may be necessary to test a large number of antigens isolated from a pathogen. Ultimately, no single antigen may prove effective as a vaccine because the ability of subunit or killed vaccine preparations to elicit a broad immune response is generally quite limited.

Certain disadvantages of conventional vaccines are overcome by using what is called "genetic immunization" (Tang, 1992). This technology involves inoculating simple, naked plasmid DNA encoding a pathogen protein into the cells of the host. The pathogen's antigens are produced intracellularly and, depending on the attached targeting signals, can be directed toward major histocompatibility complex (MHC) class I or II presentation (Ulmer, et al, 1993; Wang, et al, 1993). Risk of infection is essentially eliminated and the DNA can be delivered to cells not normally infected by the pathogen. Compared to conventional vaccines, the production of genetic vaccines is straightforward and DNA is considerably more stable than proteinaceous or live/attenuated vaccines. Genetic immunization (a.k.a. DNA, polynucleotide etc. immunization) with specific genes has shown promise in several model systems of pathogenic disease (Davis, et al, 1993; Conry, et al, 1994; Xiang, et al, 1994), and a few natural systems (Cox, et al, 1993; Fynan, et al, 1993). Use of DNA (or RNA) thus overcomes some of the problems encountered when an animal is presented directly with an antigen.

However, despite promising initial results with genetic vaccination, there remains the more basic and unsolved problem of identifying the particular gene or genes of the pathogen that will express an immunogen capable of priming the immune system for rapid and protective response to pathogen challenge. Certain non-viral pathogens and some viruses have very large genomes; for example, protozoa genomes contain up to about $10^8$ nucleotides, thus posing an expensive and time-consuming analytical challenge to identify or isolate effective immunogenic antigens. The solution to this problem to date has been to extensively study the pathobiology of the host-pathogen interaction to isolate the protein reacted to by the host during infection. And even with identification of a gene or subunit that elicits a protective immune response, there may still be lacking strong protection because of lack of broad response to the encoded polypeptide.

Significantly, the time and money to identify and develop a vaccine would be greatly reduced if there were available simple, systematic and rapid ways to identify vaccines for specific pathogens without having first to determine at least the fundamental biological properties of the pathogen. Even more important would be vaccines that are broadly effective without any danger of causing the disease against which it is intended to protect.

SUMMARY OF THE INVENTION

The present invention addresses one or more of these and other drawbacks inherent in the prior art by providing novel methods of generating and identifying effective vaccines. The vaccines stimulate a broad protective response in a manner similar to that generated by live/attenuated vaccines without the inherent disadvantage of potentially causing the disease associated with the pathogen. The invention also includes novel antigenic polypeptides encoded by DNA plasmid vaccines, kits that include antigenic pathogen polypeptides, plasmid vaccines or antibodies generated from the pathogen polypeptides.

The invention, in general terms, arises from the inventors' success in developing a way to present to an animal a major number of antigenic determinants encoded by the genome of any pathogen. The DNA of the pathogen is fragmented, ligated into expression vectors and cloned sub-libraries (sibs) of the expression library are inoculated into an animal. Sib library is understood to be a portion of a parental library that may or may not have overlapping members with other sibs of the same library. "Sibbing" as used herein is understood to mean the partitioning of a parental library into sequential subsets. Challenge by the pathogen reveals which animals are protected and consequently which portions of the sib expression library have protective effect. Sibbing methods may then be used to identify the individual or combinations of plasmids that are responsible for the protection. It is then possible to prepare vaccines from the plasmids, and to identify the polypeptides encoded by the protective plasmid vectors. One may also use well known methods to generate polyclonal or monoclonal antibodies to identified immunogens and use these as vaccines.

The invention is particularly directed to methods of vaccination. A cloned expression library is prepared from fragmented genomic DNA of a pathogen, or may be prepared from cDNA of pathogen RNA. One then introduces one or more of the library clones into an animal so as to induce an immune response against one or more of the antigens that are encoded by one or more of the clones. Subsequently, one may isolate the particular clone or clones responsible for producing an antigen that induces an immune response, obtain the antibodies, if any, generated in response to one or more of the clones, or formulate vaccine compositions from the various libraries or sib libraries that induce an immune response.

The inventors' method allows rapid screening for potential vaccines. It also allows discovery of new vaccines that would not be detected by conventional approaches. For such screening, one first selects or identifies a particular pathogen to which a protective vaccine is desired. For example, the method has been applied to a mycoplasm, *Mycoplasma pulmonis*, and to a eubacterium, *Listeria monocytogenes*. These pathogens are but two examples of the wide range of pathogens that might be screened; the method is equally adaptable to screen for vaccines for HIV, malaria, mycoplasma, tuberculosis, respiratory syncytial virus, and conjugated pneumoccus; all pathogens for which there are no effective vaccines. One may also screen for alternative and improved vaccines for diseases such as smallpox and polio. Nor is the method limited necessarily to viruses and bacteria. Use of any pathogen is contemplated, including protozoa, yeast, fungi, worms or prions. It is only necessary to obtain genomic material e.g., DNA or RNA or, in the case of prions, because they are proteins, to isolate or synthesize a DNA that encodes the prion.

After selecting the pathogen(s) to which a vaccine is desired, one then obtains a genomic or cDNA (or RNA) sample which is subsequently fragmented, for example by physical fragmentation or, preferably, by enzymatic cleavage, i.e. use of restriction endonucleases. Fragmentation methods are well known to those skilled in the art and may be varied to obtain segments (by use of different restriction endonucleases or combinations and digestion times) differing in size and composition.

After fragmentation of the DNA, an expression library is prepared. Preparation of such libraries is relatively straightforward and can be performed by well known methods. Standard cloning vectors such as Puc118 may be employed which have an ampicillin selectable marker and, preferably ori and a CMV promoter. Bacteria are then transformed with the vectors, for example, *E. coli* or Salmonella or other suitable bacterial host. Identified transformants are cultured by standard procedures and the plasmid DNA isolated by such methods as chromatographic or organic separation. A series of plasmids have been constructed which allow cloning each library into a site which can direct the foreign protein to MHCI or II. These plasmids are shown in FIG. 1.

For prions, a relatively rare class of pathogens, a preferred method is to determine the amino acid sequence of the protein and synthesize the encoding DNA, or, alternatively, isolate encoding DNA from infected cells. The prion-encoding DNA is then fragmented and used to prepare an expression library in a manner analogous to that of RNA, cDNA or genomic DNA.

An important aspect of the invention is the preparation of a representative expression library from pathogen DNA. *Mycoplasma pulmonis* is one example of a pathogen. MP has a genome size of $\sim 1 \times 10^6$ bp. Two of nine sib libraries provided protective and were thus identified as candidates for effective vaccine protection. Each sib library had $\sim 3 \times 10^3$ members, of which only $\sim 500$ should be expressing natural open-reading frames. That two libraries protected indicated that several plasmids or combinations of plasmids were vaccine candidates. It appears likely that a minimal number of plasmids will provide useful protection. Tests of two smaller MP libraries of $\sim 70$ members derived from MP2.3 showed little or no protection, from which it was concluded that the protective plasmid(s) are located in other sub-libraries of MP2.3. The inventors have shown that the disclosed expression libraries can be used directly as vaccines or partitioned in various ways to isolate individual or combinations of plasmids that are protective. In this way the ELI technology is a practical vaccine discovery approach, even for protein subunit vaccines.

As mentioned, DNA is fragmented either physically or, for example, by restriction enzymes, to produce relatively small pieces, preferably on the order of 100 to 1,000 base pairs. For smaller genomes, several hundred base pairs are preferable, for example, 400 hundred base pairs; however, larger genomes, such as found in Pseudomonas or *E. coli* might initially be fragmented into somewhat larger sizes, for example, 3000–4000 bp. Except in the case of extremely small genomes, a preferred method of practice is to prepare sib libraries from the main expression library. For example, a library including DNA mean fragment sizes of approximately 400 bp are preferably sibbed into sublibraries containing approximately 3000 transformants, i.e. approximately 21 sublibraries. A smaller number of sublibraries, or sib libraries, is preferred for smaller genomes, such as mycoplasma, where a 3000 member library is achieved with approximately 9 sib libraries.

Of course it is technically feasible to apply ELI to any pathogens with larger genomes. Genomes smaller than Mycoplasm and Listeria, many of which have genomes up to 100-fold smaller than Mycoplasm, are well-suited for application of the disclosed methods of identifying and isolating immunogens. These pathogens include HIV, known to have an exceptional number of variants and which is therefore an excellent candidate for screening with the ELI.

Genetic immunization with the ELI expression library reproduces the same antigens induced by a live/attenuated pathogen, i.e., the entire genome. Additionally, and importantly, the method is such as to allow presentation of new determinants that are normally hidden by the biology of the pathogen. The new ELI method combines the advantages of genetic immunization without the necessity of discovering a single protective gene or foreknowledge of the pathogen's biology.

Once expression libraries have been prepared for a given pathogen and DNA plasmid libraries isolated, one will inoculate a mammal with a DNA plasmid library. The library may be inoculated into the animal in any one of several different methods that have been shown effective for genetic immunization; for example, gene gun or needle injection into muscle or skin or by oral administration. The gene gun technique used for ELI is thought to be approximately 1,000- to 10,000-fold more efficient than injection of naked DNA (Fynan, et al. (1993)). Alternatively, others e.g Ulmer et al. (1993), have indicated the genetic immunization by direct DNA injection may be performed with similar efficiency as the gene gun. The inventors have found that gene administration by either method produces qualitatively identical immunization.

The inventors' method has broad application as a screening method for identifying vaccines. Briefly, this involves preparing an expression library from fragmented genomic nucleic acid, isolating plasmid DNA and immunizing with at least a portion of the library. A protective effect is indicated when an animal is challenged with the pathogen from which the genomic material was obtained.

The inventors have found that mammalian genes fused to the pathogen DNA appears to facilitate expression in the mammalian cell. In preferred embodiments, a mammalian gene such as that encoding human growth hormone is fused with the DNA; however, other genes would be suitable, including a-trypsin, ubiquitin or signal sequences. The inventors have found that fusion of nonmammalian pathogen sequences to mammalian genes increases the amount of antigen available to the immune system. This may arise because of increasing antigenic recognition or targeting to components in the cell.

The inventors have found that the maximum expression by genetic immunization (ELI) is obtained when about 2.5 mg is introduced per site of inoculation when gene gun inoculation is used. Different amounts may be required if other methods of introduction are employed. The inventors have also determined that the lowest amount of DNA that produces an immune response is between about 0.1 and 1 ng. (FIG. 2). This was shown by injecting various amounts of human growth hormone DNA into mice and monitoring antibody production. Antibody was detectable with 1 ng. It was thus predicted that the maximum complexity represented by inoculating 10 mg (in four sites) of a library under these conditions such that an immune response would be generated comprising approximately $1 \times 10^4$ clones (or $1/6 \times 1 \times 10^4 = 1.5 \times 10^3$ expressing clones). This indicated that approximately $1 \times 10^4$ clones could be included in each sib library. An inoculation of approximately 10 mg of DNA would introduce the equivalent of approximately $10^9$ bacterial genomes into the host in a highly immunogenic form. This exceeds by several orders of magnitude the number of genome equivalents generally necessary to produce infection in a host. For example, mycoplasma can produce an infection when inoculated at $10^3$ to $10^6$ organisms per animal. These results were an important aspect of the invention because there was a real question whether these predictions concerning the number of plasmids that could be injected would actually be feasible. Had large libraries not been shown to be protective, there would have been little value to the disclosed methods.

Genetic immunization procedures are now well established and well known in the art. One or more inocula of the library aliquots may be employed for immunization. Likewise, vaccine compositions may vary widely, to include for example various adjuvants.

ELI is expected to elicit response of both arms of the immune system. Extracellular antigens are largely presented through MHCII proteins and produce a humoral defense, i.e., circulating antibodies against proteins of the pathogen. Intracellular pathogens present proteins through a different pathway that goes through the endoplasmic reticulum and onto MHCI proteins to elicit the cellular arm of the immune system. For many pathogens, the relative importance of the two arms in protection is not known and the two systems may crossover in macrophages and through natural immunity, e.g., natural killer cells. Use of appropriate vectors may cause one or both of the immune responses to be favored.

The inventors have shown that ELI will produce a vaccine without knowing what specific protein(s) is responsible for eliciting protection. In this sense ELI mimics live/attenuated vaccines. Another advantage over conventional vaccines is that peptides may be presented to the immune system with ELI which are normally hidden by the pathogen's biology or immune-avoidance mechanisms. Unlike live/attenuated vaccines where the stoichiometry of the pathogen's antigens is fixed, the composition of the library can be modified at will to allow introduction of only the most effective antigens at varied levels. By using ELI, the site of inoculation can be controlled allowing cells not normally infected to present antigens. In addition, use of other fusion proteins than hGH should allow antigens to be targeted to specific presentation pathways.

The effective protection against mycoplasm demonstrated by the inventors indicated both humoral and cellular responses were elicited. Previous work demonstrated that anti-mycoplasma antibodies can protect mice against infection (Tayler, et al, 1981), yet passive transfer of antibody does not protect rats (Davidson, et al, 1982). Immune spleen cells, however, can transfer protection in syngeneic rats (Cassell, 1982; Lai, et al, 1991). It has also been demonstrated in mice that augmented natural killer cells or secreted interferon gamma-activated macrophages can kill mycoplasma (Lai, et al, 1990). Given this uncertainty about the relative contributions to resistance and the fact that both responses were elicited with the library inoculations, the strong protection does not appear to arise primarily from one or the other immune arm. This aspect is very attractive, as it indicates a broad protective response from ELI immunization.

ELI is expected to elicit immunity against any organisms requiring either arm of the immune system because it activates both humoral and cellular immune responses. The protection afforded is therefore quite broad and is expected to provide superior protection compared with single antigen or antigen-encoding DNA.

The invention also contemplates that the disclosed DNA libraries or the peptides encoded by identified protective DNA plasmids will be useful in developing a wide range of vaccines and will also be useful in certain methods of cancer treatment. Cancer treatment methods, including vaccine development are another aspect of the present invention. Additionally, a variety of in vitro and in vivo assay protocols are facilitated as a result of the novel compositions disclosed herein. In addition to generating an immune response in an animal, and particularly in a human, the peptides may also be used as immunogens to generate anti-peptide antibodies, which themselves have many uses, not least of which is the detection of pathogen related peptides, or peptide fragments thereof, in diagnostic tests and kits based upon immunological binding assays).

Therefore, one contemplated use for the pathogen peptides concerns their use in methods for detecting the presence of a pathogen within a sample. These methods include contacting a sample suspected of containing a pathogen with a peptide or composition in accordance with the present invention under conditions effective to allow the peptide(s) to form a complex with pathogen-related peptides contained in the sample. One then detects the presence of the complex by detecting the presence of the peptide(s) within the complex, e.g., by either originally using radiolabeled peptides or by subsequently employing anti-peptide antibodies and standard secondary antibody detection techniques.

The peptides, or multimers thereof, may be dispersed in any one of the many pharmacologically-acceptable vehicles known in the art and particularly exemplified herein. As such, the peptides may be encapsulated within liposomes or incorporated in a biocompatible coating designed for slow-release. The preparation and use of appropriate therapeutic formulations will be known to those of skill in the art in light of the present disclosure. The peptides may also be used as part of a prophylactic regimen designed to prevent, or protect against, disease pathogens, possible cancer progression and/or metastasis and may thus be formulated as a vaccine.

The present invention also provides methods for identifying specific pathogen peptides, which methods comprise contacting the cells suspected of containing such polypeptides with an immunologically effective amount of a composition comprising one or more specific anti-peptide antibodies disclosed herein.

In another aspect, the present invention contemplates a diagnostic kit for screening samples suspected of containing pathogen polypeptides, or cells producing such polypeptides. Said kit can contain a peptide or antibody of the present invention. The kit can contain reagents for detecting an interaction between an agent and a peptide or antibody of the present invention. The provided reagent can be radio-, fluorescently- or enzymatically-labeled. The kit can contain a known radiolabeled agent capable of binding or interacting with a peptide or antibody of the present invention.

In another aspect, the present invention contemplates a diagnostic kit for detecting mycoplasm or Listeria polypeptides. The kit comprises reagents capable of detecting such peptides. The provided reagent may also be radio-, enzymatically-, or fluorescently-labeled. The kit can contain a radiolabeled peptide capable of binding to or interacting with a mycoplasma or Listeria polypeptide, or, preferably, may contain a radiolabeled antibody capable of binding to or interacting with a peptide of the present invention. The kit can contain a polynucleotide probe that encodes a peptide of the present invention or any of their complements. The kit can contain an antibody immunoreactive with a peptide of the present invention.

The reagent of the kit can be provided as a liquid solution, attached to a solid support or as a dried powder. Preferably, when the reagent is provided in a liquid solution, the liquid solution is an aqueous solution. When the reagent provided is attached to a solid support, the solid support can be chromatograph media, a test plate having a plurality of wells, or a microscope slide. When the reagent provided is a dry powder, the powder can be reconstituted by the addition of a suitable solvent, optionally provided.

In still further embodiments, the present invention concerns immunodetection methods and associated kits. It is proposed that the peptides of the present invention may be employed to detect antibodies having reactivity therewith, or, alternatively, antibodies prepared in accordance with the present invention, may be employed to detect pathogen polypeptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For diagnostic purposes, it is proposed that virtually any sample suspected of comprising either the mycoplasma or Listeria or antibody sought to be detected, as the case may be, may be employed. Exemplary samples include clinical samples obtained from a patient or animal such as blood or serum samples, ear swabs, sputum samples, middle ear fluid or even perhaps urine samples may be employed. Furthermore, it is contemplated that such embodiments may have application to non-clinical samples, such as in the titering of antigen or antibody samples, in the selection of hybridomas, and the like.

In related embodiments, the present invention contemplates the preparation of kits that may be employed to detect the presence of pathogen peptides and/or antibodies in a sample. Generally speaking, kits in accordance with the present invention will include a suitable antigenic peptide, e.g from mycoplasma or Listeria, or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container means will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

BRIEF DESCRIPTION OF THE DRAWINGS

FIG. 1. Examples of ELI vectors to direct antigens for different MHC class presentation. Secreted antigens are expected to favor MHC class presentation and antibody production. Cytoplasmic or proteasomal-directed antigens should favor MHC class I presentation and CD8+ cytotoxic T lymphocyte activation.

DESCRIPTION OF ILLUSTRATIVE EMBODIMENTS

Figure 2:
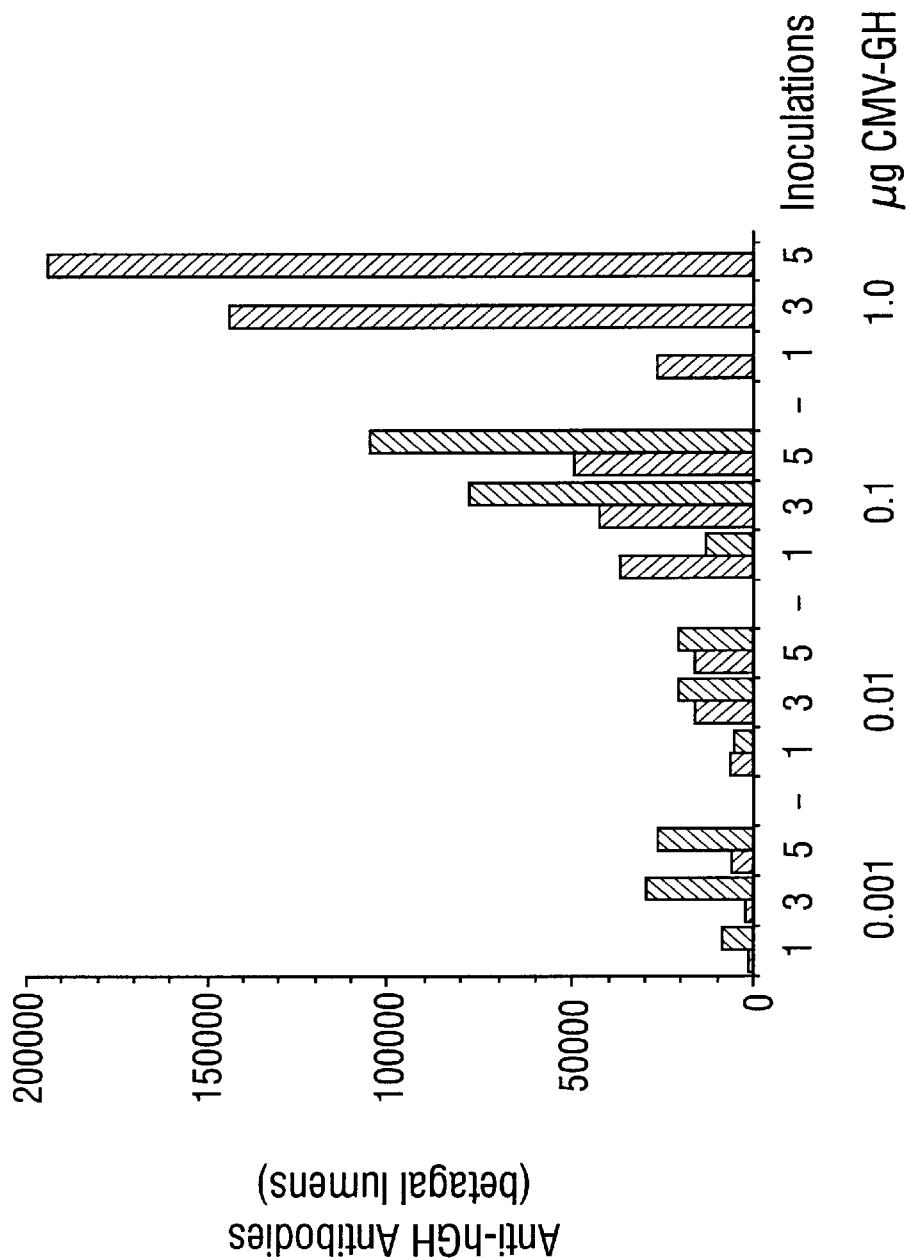
FIG. 2. hGH antibodies produced by genetic immunization with varied amounts of CMV-GH plasmid. 5–6 week old female Balb/C mice were inoculated every two weeks in 2 shots with the gene gun using the indicated amounts of CMV-GH plasmid. Each inoculum under 1 mg was balanced to 1 mg with CMV-LUC, a luciferase expression plasmid. Inoculations indicates samples of sera collected 10 days after the indicated CMV-GH inoculation. The entire set of sera along with pre-immune sera was tested by b-galactosidase ELISA. Anti-hGH Antibodies (betagal lumens) represents the ELISA lumens produced by each sample minus the pre-immune background. The black and striped bars for each different amount of CMV-GH represents an individual mouse tested.

The invention includes a novel expression library immunization (ELI) method applicable to virtually any pathogen and that requires no knowledge of the biological properties of the pathogen. The method operates on the assumption, generally accepted by those skilled in the art, that all the potential antigenic determinants of any pathogen are encoded in its genome. The inventors have now devised methods of identifying vaccines using a genomic expression library representing all of the antigenic determinants (except for those resulting from modification of the protein) of a pathogen. The method has the advantages of "gene immunization" by eliminating potential for infection while also providing for the first time a general and effective method of immunizing and identifying a vaccine without having to characterize the pathogen against which the vaccine is desired.

The preparation of an expression library is performed using the techniques and methods familiar to the molecular biologist. The pathogen's genome, whether bacterial, yeast, mold, fungal, algal, protozoan, viral, may or may not be known and may even have been cloned. Thus one obtains DNA (or cDNA), representing substantially the entire genome of the pathogen. The DNA is broken up, by physical fragmentation or restriction endonuclease, into segments of some length so as to provide a library of about $10^{-1}$ (×genome size) members. Of course for cloned DNA in YACs, a sufficient library may be available. In cases, as for certain viruses, where the genome is RNA, the RNA may be used to prepare a DNA library. Alternatively, mRNA may be used to generate libraries; for example from human or animal tumor cells.

The in vivo effectiveness of the novel immunization has been demonstrated with genomes differing in size by approximately four-fold. The inventors have demonstrated ELI protection against Mycoplasma pulmonis with a genome of ~$1 \times 10^6$ bp and have also shown protection against Listeria monocytogenes, a pathogen whose genome is approximately $4 \times 10^6$ bp. These pathogens represent two different classes of pathogens, Mollicutes and Gram-positive bacilli respectively and serve to demonstrate the broad applicability of the method.

One expects the disclosed techniques and methods to apply not only to the Listeria and Mycoplasma genera but also to the broader classes of pathogens including Mollicutes and Gram-positive bacilli. Numerous species comprise the genera of these classes, including the unusual asporogenous aerobic bacilli represented by Rothia, *kurthia* and Oerskovia. Most pathogens have genomes the same or smaller size than Listeria or Mycoplasma and the method will also apply to larger genomes and will be suitable for developing and identifying vaccines from broad categories of human and non-human pathogens, shown in Table 1.

TABLE 1

| | |
|---|---|
| viruses | genome of ~$10^3$ to $10^5$ bp |
| mycoplasma | genome of ~$10^6$ bp |
| bacteria | genome of ~$2 \times 10^6$ to $9 \times 10^6$ bp |
| Fungi | genome of ~$2 \times 10^7$ bp |
| Algae | genome of ~$5 \times 10^7$ bp |
| Protozoa | genome of ~$5 \times 10^7$ bp |
| Molds | genome of ~$5 \times 10^7$ bp to $9 \times 10^7$ bp |
| cDNA library (any pathogen or cancer) | ~$10^3$ to $10^6$ bp |
| mitochondrial genome | ~$10^4$ to $10^5$ bp |

1. Other Methods of Inoculation

Introducing an expression library into a subject may be performed in several ways; including by gene gun. The gene gun technique used for ELI is thought to be ~1000 to 10,000-fold more efficient than injection of naked DNA (Fynan, et al (1993). Others, e.g. Ulmer, et al (1993) have indicated that genetic immunization by direct DNA injection may be performed with similar efficiency as the gene gun. The inventors have found that gene administration by either method produces qualitatively identical immunization. The expression library may also be introduced by methods other than genetic immunization. The bacteria bearing the library can be directly inoculated into the host or the library and put into an infectious agent, such as adenovirus. Once the protecting pathogen gene(s) has been isolated the actual vaccine can be by genetic immunization.

Of course, in light of the new technology on DNA vaccination, it will be understood that virtually all such vaccination regimens will be appropriate for use with DNA vectors and constructs, as described by Ulmer et al. (1993), Tang et al. (1992), Cox et al. (1993), Fynan et al. (1993), Wang et al. (1993) and Whitton et al. (1993), each incorporated herein by reference. In addition to parenteral routes of DNA inoculation, including intramuscular and intravenous injections, mucosal vaccination is also contemplated, as may be achieved by administering drops of DNA compositions to the nares or trachea. It is particularly contemplated that a gene-gun could be used to deliver an effectively immunizing amount of DNA to the epidermis (Fynan et al., 1993).

2. ELISAs

ELISAs may be used in conjunction with the invention. In an ELISA assay, proteins or peptides incorporating pathogen antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tweene®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

3. Epitopic Core Sequences

The present invention is also directed to protein or peptide compositions, free from total cells and other peptides, which comprise a purified protein or peptide which incorporates an epitope that is immunologically cross-reactive with one or more pathogen antibodies, for example those polypeptides that comprise the epitopic regions of mycoplasma or Listeria genome.

As used herein, the term "incorporating an epitope(s) that is immunologically cross-reactive with one or more pathogen antibodies" is intended to refer to a peptide or protein antigen which includes a primary, secondary or tertiary structure similar to an epitope located within any of a number of pathogen polypeptides encoded by the pathogen DNA or RNA. The level of similarity will generally be to such a degree that monoclonal or polyclonal antibodies directed against the such polypeptides will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of pathogen epitopes, and/or their functional equivalents, suitable for use in vaccines is part of the present invention. Once isolated and identified, one may readily obtain functional equivalents. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will depend on the particular peptides identified from sib library immunization, as disclosed herein. Relatively short peptides, such as those prepared from 8 to 30 or so amino acids may provide advantages in certain circumstances, for example, in the preparation of some vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to pathogen-specific peptide sequences. These epitopic core sequences are identified herein in particular aspects as hydrophilic regions of the pathogen antigens. It is proposed that these regions represent those which are most likely to promote T-cell or B-cell stimulation or humoral response, and, hence, elicit specific antibody production.

An epitopic core sequence, as used herein, is a relatively short stretch of amino acids that is "complementary" to, and therefore will bind, antigen binding sites on transferrin-binding protein antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of up to several tens of amino acids, depending on the size of the DNA found to in the protective plasmid identified by using the expression library immunization method. Thus, this size will generally correspond to the smallest peptide antigens prepared in accordance with the invention. However, the size of the antigen may be relatively large, for example up to several hundred or more where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson & Wolf, 1988; Wolf et al., 1988). Computerized peptide sequence analysis programs (e.g., DNAStar Software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4. Immunoprecipitation

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

5. Western Blots

The compositions of the present invention may find use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the peptide moiety are considered to be of particular use in this regard.

6. Vaccines

The present invention contemplates vaccines for use in both active and passive immunization embodiments. Immunogenic compositions, proposed to be suitable for use as a vaccine, may be prepared most readily directly from immunogenic pathogen sib expression libraries in the manner disclosed herein. Preferably the antigenic material is extensively dialyzed to remove undesired small molecular weight molecules and/or lyophilized for more ready formulation into a desired vehicle. Vaccines may be polypeptide or DNA compositions. DNA compositions are preferably cloned sib expression libraries, obtained from the fragmented genome of a pathogen.

The inventors have demonstrated that one may generate an immune response in an animal by administering to the animal, or human subject, a pharmaceutically acceptable composition comprising an immunologically effective amount of a cloned expression nucleic acid library. The stimulation of specific antibodies and CTL (cytotoxic T lymphocyte) responses upon administering to an animal a nucleic molecule is now well known in the art, as evidenced by articles such as Tang et al. (1992); Cox et al. (1993;) Fynan et al. (1993); Ulmer et al. (1993); Wang et al. (1993) and Whitton et al. (1993); each incorporated herein by reference.

This technology, often referred to as genetic immunization, is particularly suitable to protect against bacterial infections and is expected to be equally protective against viral infections. Indeed, immunization with DNA has been successfully employed to protect animals from challenge with influenza A (Ulmer et al., 1993). Therefore, the use of the expression library compositions of the present invention employing techniques similar to those described by Ulmer et al. (1993, incorporated herein by reference), is considered to be particularly useful as a vaccination regimen.

The expression library DNA segments can be used in virtually any form, including naked DNA and plasmid DNA, and may be administered to the animal in a variety of ways, including parenteral, mucosal and gene-gun inoculations, as described, for example, by Fynan et al. (1993) and Tang et al (1992).

The inventors have used expression plasmids for immunization; however, it is contemplated that the DNA segments themselves as immunizing agents to vaccinate against infection and disease. The technology for using DNA segments as vaccines has recently been developed and is generally termed "Genetic Immunization" or "DNA Vaccination" (Cohen, 1993). It is now known that cells can take up naked DNA and express the peptides encoded on their surface, thus stimulating an effective immune response, which includes the generation of cytotoxic T lymphocytes (killer T cells).

The utilization of this technology, and variations thereof, such as those described by Tang et al. (1992), Ulmer et al. (1993); Cox et al. (1993), Fynan et al. (1993), Wang et al. (1993) and Whitton et al. (1993), each incorporated herein by reference, is particularly suitable as it has already been shown to be successful against a form of influenza virus, the type of pathogen also targeted by the present invention. It is contemplated that virtually any type of vector, including naked DNA in the form of a plasmid, could be employed to generate an immune response in conjunction with a wide variety of immunization protocols, including parenteral, mucosal and gene-gun inoculations (Tang et al, 1992; Fynan et al., 1993).

The preparation of vaccines which contain peptide sequences, determined from the DNA of plasmids identified as protective against pathogen challenge, as active ingredients is generally well understood in the art, as exemplified by U.S. Pat. Nos. 4,608,251; 4,601,903; 4,599,231; 4,599,230; 4,596,792; and 4.578,770, all incorporated herein by reference. Typically, such vaccines are prepared as injectables, either as liquid solutions or suspensions or solid forms suitable for solution in, or suspension in, liquid prior to injection. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like These compositions take the form of solutions, suspensions, tablets, pills, capsules, sustained release formulations or powders and contain about 10 to about 95% of active ingredient, preferably about 25 to about 70%.

The pathogen peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include gene gun inoculation of the DNA encoding the antigen peptide(s), phage transfection of the DNA, oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

7. DNA Segments Encoding Novel Peptides

The present invention also concerns DNA segments, that can be isolated from virtually any non-mammalian pathogen source, that are free from total genomic DNA and that encode the novel peptides disclosed herein. DNA segments encoding these peptide species may prove to encode proteins, polypeptides, subunits, functional domains, and the like of pathogen or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a pathogen peptide refers to a DNA segment that contains these peptide coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified pathogen peptide-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case, a gene encoding pathogen epitopes of polypeptides forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode pathogen antigenic species that includes within its amino acid sequence an amino acid sequence that essentially include one or more amino acid sequences of epitopic regions of the pathogen polypeptide.

It will also be understood that amino acid and nucleic acid sequences may include additional residues, such as additional N- or C-terminal amino acids or 5¢ or 3¢ sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5¢ or 3¢ portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding any of the immunogenic polypeptide sequences identified by the methods herein disclosed, or that are identical to or complementary to DNA sequences which encode any of these peptides.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 10,000 nucleotides and the like.

It will also be understood that this invention is not limited to the particular nucleic acid sequences which encode peptides of Mycoplasma or Listeria or only to pathogen DNA encoding only epitopic regions. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full-length protein or smaller peptide, is positioned under the control of a promoter. The promoter may be in the form of the promoter that is naturally associated with a gene encoding peptides of the present invention, as may be obtained by isolating the 5¢ non-coding sequences located upstream of the coding segment or exon, for example, using recombinant cloning and/or PCRÔ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a pathogen peptide in its natural environment. Such promoters may include promoters normally associated with other genes, and/or promoters isolated from any bacterial, viral, eukaryotic, or mammalian cell. Naturally, it will be important to employ a promoter that effectively directs the expression of the DNA segment in the cell type, organism, or animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment. An appropriate promoter for use in high-level expression is the cytomegalovirus promoter (Pharmacia LKB Biotechnology), although one is not limited to use of this promoter.

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of pathogen epitopic core regions, such as may be used to generate anti-peptide antibodies, also falls within the scope of the invention. DNA segments that encode peptide antigens from about 8 to about 50 amino acids in length, from about 8 to about 30 amino acids in length, or even from about 8 to about 20 amino acids in length are contemplated to be particularly useful.

In addition to their use in directing the expression of the pathogen peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to peptide-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequences of any of the DNAs disclosed, are contemplated as hybridization probes for use in, e.g., Southern and Northern blotting. Smaller fragments will generally find use in hybridization embodiments, wherein the length of the contiguous complementary region may be varied, such as between about 10–14 and about 100 nucleotides, but larger contiguous complementarity stretches may be used, according to the length complementary sequences one wishes to detect.

The use of a hybridization probe of about 10–14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCRÔ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of 50° C. to 70° C. Such selective conditions tolerate little, if any, mismatch between the probe and the template or target strand. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1993; Segal 1976; Prokop, 1991; and Kuby, 1991, are particularly relevant.

Of course, for some applications, for example, where one desires to prepare mutants employing a mutant primer strand hybridized to an underlying template or where one seeks to isolate pathogen peptide-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

8. Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

9. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

10. Monoclonal Antibody Generation

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified epitopic protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5'10^7$ to $2'10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp.65–66, 1986; Campbell, pp.75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71–74, 1986).

Fusion procedures usually produce viable hybrids at low frequencies, about $1'10^{-6}$ to $1'10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immuno-binding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Vector Constructs. CMV-GH was constructed by insertion of the genomic hGH sequence from CMV-GH-ori (Barry et al, 1994) as a BamHI fragment into the BglII site of CMV5, a derivative of CMV1 (Andersson et al, 1989)]. CMV-GH-F1&3 was constructed by knocking out the BamHI in CMV-GH and inserting the annealed, kinased oligonucleotides, GATCTTGGATCCTAAGTAAGTA (SEQ ID NO:1) and AGCTTACTTACTTAGGATCCAA (SEQ ID NO:2), into BglII-HindIII-digested CMV-GH. CMV-GH-F2 was constructed similarly by inserting the oligos, GATCG-GATCCTAAGTAAGTA (SEQ ID NO:3) and AGCTTACT-TACTTAGGATCC (SEQ ID NO:4) in BglII-HindIII-digested CMV-GH. *Mycoplasma pulmonis* strain CT was grown in Chalquest media for isolation of genomic DNA. *Listeria monocytogenes* was grown in LB. Genomic DNA was isolated from each as described Ausubel, 1992. Each genomic DNA was partially digested with MboI to an approximate mean fragment size of 0.5 kilobase pairs. CMV-GH-F1&3 and CMV-GH-F2 were digested with BamHI or BglII and dephosphorylated with shrimp alkaline phosphatase. Each vector was ligated with a 5-fold excess of genomic MboI fragments and electroporated into TG1 bacteria. Transformant number was estimated by plating serial dilutions onto YT-ampicillin plates and approximately 3000 transformants were grown overnight in LB-ampicillin and frozen. 5 ml of this overnight grow up was used to inoculate a 500 ml LB-amp culture from which plasmid DNA was prepared using Qiagen plasmid purification columns.

Animals. Mice were treated in accordance with institutional guidelines. Prior to immunization, the mice were anesthetized with 0.5 ml of avertin i.p. and their ears depilated with NairÔ. Up to 2.5 mg of plasmid DNA was loaded on 0.5 mg of 1–3 mm gold microparticles for each inoculum. The total amount of DNA to be delivered was delivered in 4 inoculums into both sides of both ears using the hand-held biolistic gene gun described in Sanford, et al, 1991.

Measurement of Delayed-type Hypersensitivity (DTH). DTH was evaluated by injecting PBS into the right rear footpad and PBS containing 50 mg sonicated MP cell protein into the left rear footpad. A dial gauge caliper was used to measure the change in footpad thickness induced 24 h after injection. Three readings were measured and averaged.

Macrophage Migration Inhibition (MMI). MMI was evaluated by filling a glass capillary tube with 100 ml of spleen cell suspension ($1\times10^8$ cells/ml) from each mouse and placing it horizontally in a well of a 24 well plate immersed in RPMI media in the absence or presence of 50 g/ml sonicated MP protein. After 24 h, the area of cell migration out of the tube was measured by digital imaging. The area of migrated cells from control animal was averaged. Less migration was indicative of release of MIF from T-cells previously activated against MP antigens by immunization. Release of MIF in this assay results in reduced area of migrated cells from the capillary.

EXAMPLE 1

This example illustrates that a diverse library of plasmids can be inoculated and still produce an immune response to each encoded antigen. Theoretically a library including all the genome could be inoculated, exposing the host to all the pathogen's proteins. However, inoculation with 1 mg of a library of 10,000, for example, would result in delivery of only 0.1 ng of each individual plasmid. This demonstration was important for addressing the feasibility of ELI. Previous work had shown that inoculation of 1 mg of DNA encoding hGH produced only approximately 0.1 ng of protein. Typical procedures for immunization utilize 10–100 mg of protein.

Determination of Amount Required for Immune Response

Mice were inoculated with various amounts of DNA encoding human growth hormone (hGH) and tested for antibodies against hGH (FIG. 2). Considering the need for efficiency, the gene gun was used rather than needle injection into muscle or dermis, since the gene gun appears to require less DNA for a given response (Fynan et al. 1993).

Mouse sera was recovered by tail vein bleed 10 days after gene inoculation. hGH antibodies were measured by a modified ELISA protocol which makes use of the highly sensitive, wide range, luminescent b-galactosidase assay (GalactolightÔ-Tropix) able to detect fg to ng of b-galactosidase activity.

100 ng of hGH protein in 100 ml PBS (137 mM NaCl, 2.7 mM KCl, 8.2 mM $Na_2HPO_4$, 1.5 mM $KH_2PO_4$, pH 7.4) was coated into each well of a 96 well plate ELISA plate for 2 h at room temp. The wells were blocked by the addition of 300 ml of 5% dried milk in TBST (150 mM NaCl, 10 mM Tris, pH 8, 0.1% Tween) for 1 h. The wells were washed 3 times with TBST and 200 ml of a 1/250 dilution of mouse sera was added for 2 h at room temp. This solution was removed, the wells were washed 6 times with TBST and 200 ml of a 1/1000 dilution of goat anti-mouse IgG-b-galactosidase conjugate in TBST was added for 1 h. The wells were washed 5 times in TBST and once with PBS. 200 ml of complete Galacto-light reaction buffer (1/100 dilution of galacton concentrate in reaction buffer) was added to each well and incubated for 30 to 60 min at room temp. This solution was then transferred to luminometer cuvettes, 300 ml of Galactolight accelerator was added and luminescence was measured 5 sec later by integration for 10 sec on a Berthold BIOLUMAT 9500C luminometer. Relative antibody titers are expressed in b-galactosidase lumens (FIG. 2).

Surprisingly, antibodies were detectable following inoculation of as little as 1 ng of hGH DNA, consistent with previous reports (Eisenbraun, et al, 1993). This indicated that libraries of at least $10^3$–$10^4$ members were possible with 1 mg of DNA.

EXAMPLE 2

Expression library immunization in mice was tested using the pathogen *Mycoplasma pulmonis* (MP), a wall-less bacteria. MP has a relatively small genome of ~$10^6$ base pairs (Neimark and Lange, 1990). MP is an extracellular pathogen that colonizes the lungs and other tissues (Lindsey et al, 1978). This bacterium was considered to pose a challenge for creating a representative library because it has an unusual codon usage (i.e. the tryptophan codon of MP is a stop in mammalian cells (Yamao et al, 1985) so that it appeared problematical that wider range expression of a library would be possible in mammalian cells. Additionally, MP is an endogenous pathogen in rodents (Cassell, 1982), often causing losses in animal supply colonies, and any effective vaccine discovered would be a potential benefit to those maintaining large rodent colonies.

Mycoplasm vaccination with a Mycoplasm Sib Library

Figure 3:
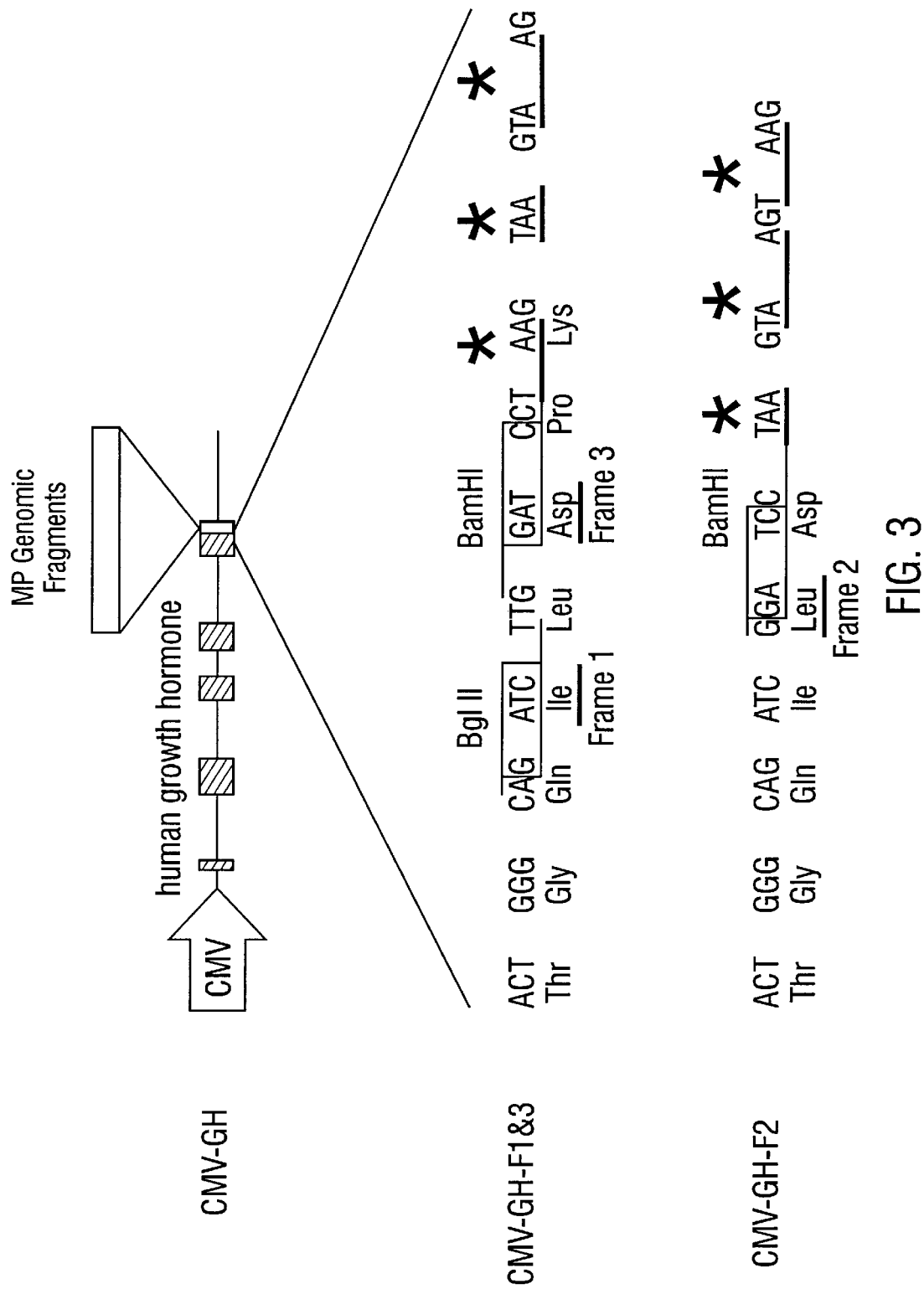
FIG. 3. Vectors used for expression library immunization (ELI). CMV-GH-F1&3 was derived from CMV-GH in which the cytomegalovirus promoter drives expression of the genomic human growth hormone (hGH) gene. CMV-GH-F1&3 differs from the hGH sequence by substitution of a BamHI site 3' to the BglII site such that restriction fragments having GATC 5' overhangs (i e. MboI fragments) can be inserted into BamHI or BglII in two different coding frames. TAA stop codons were inserted in all three coding frames 3' to both insertion sites to stop translation of any inserts lacking their own stop codons. CMV-GH-F2 was constructed similarly by knocking out the BglII site in hGH and inserting a BamHI in frame 2.

A library was constructed by inserting partially digested MP DNA into the last exon of the hGH gene under control of the CMV promoter. The hGH gene contains a signal sequence allowing MP antigens to be secreted as fusion proteins. Since the fragments of MP DNA inserted randomly, only ⅙ of the ones corresponding to open reading frames would be expected to be in-frame. To include all possible antigens, MP fragments were fused into 3 different frames of hGH sequence and with stop codons in 3 frames at the 3' end (FIG. 3). Nine independent (sib) libraries were constructed, each with ~3000 members. Over 95% of the plasmids bore inserts with a median size of ~400 bp.

Figure 4A:
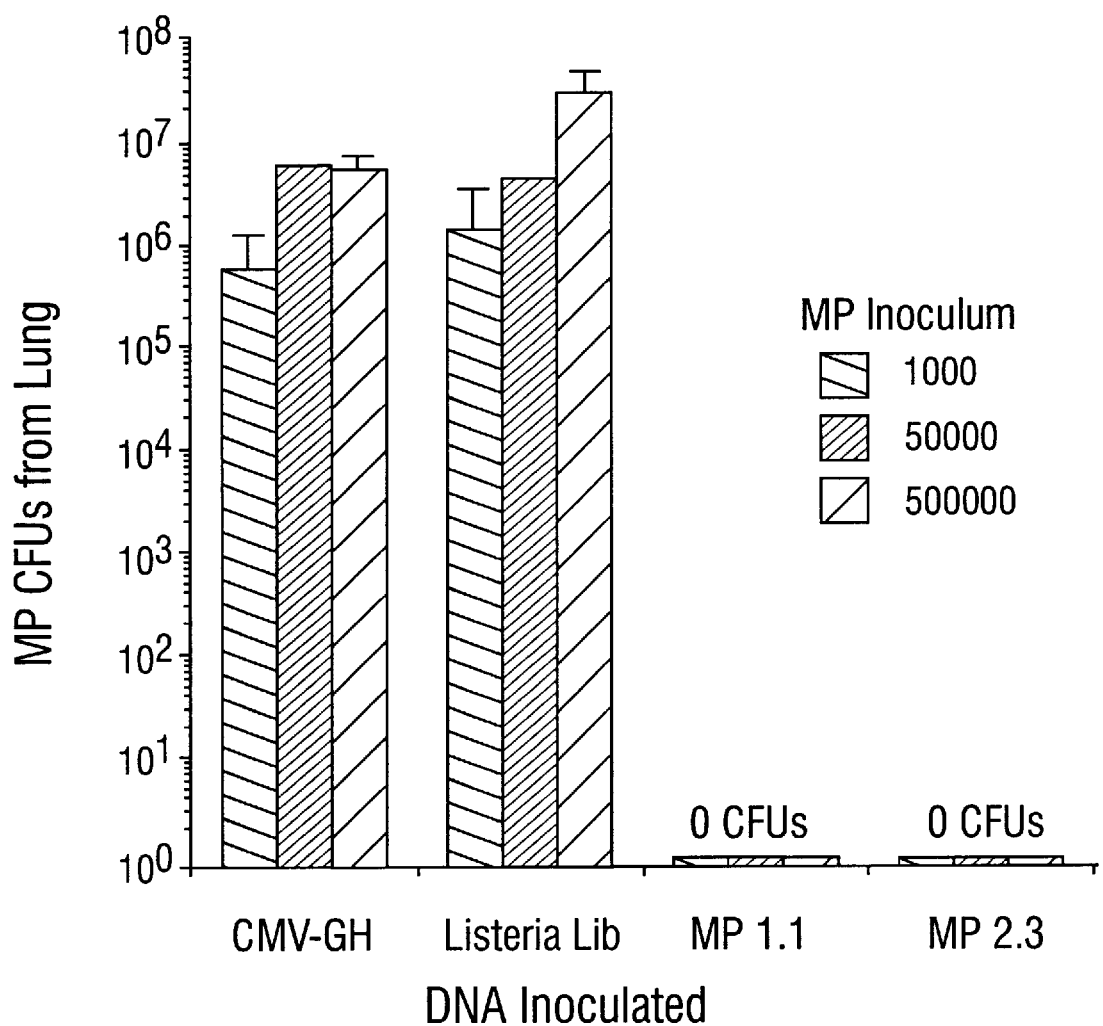
FIG. 4A. MP titers from the lungs of ELI-immunized, MP-challenged mice. 5–6 week old Balb/C female mice were immunized 4 times with 10 mg of MP1.1 and MP2.3 on day 1 and with 5 mg on day 8, 21, and 52 and challenged with the indicated number of MP (MP Inoculum) 12 days later (Lai et al, 1991). CMV-GH and listeria library mice were immunized on a similar schedule and challenged at the same time. The listeria library mice consists of a 3000 transformant library constructed into CMV-GH-F2 using MboI-digested Listeria monocytogenes genomic DNA. The mice were sacrificed 14 days after challenge and lung lavage and lung sectioning was performed. MP Titers from the lungs of ELI-immunized, MP-challenged mice. MP CFUs from Lung represents the total number of MP from each group of mice as calculated from counting MP grown on plates from serial dilutions of lung lavages from the mice.
Figure 4B:
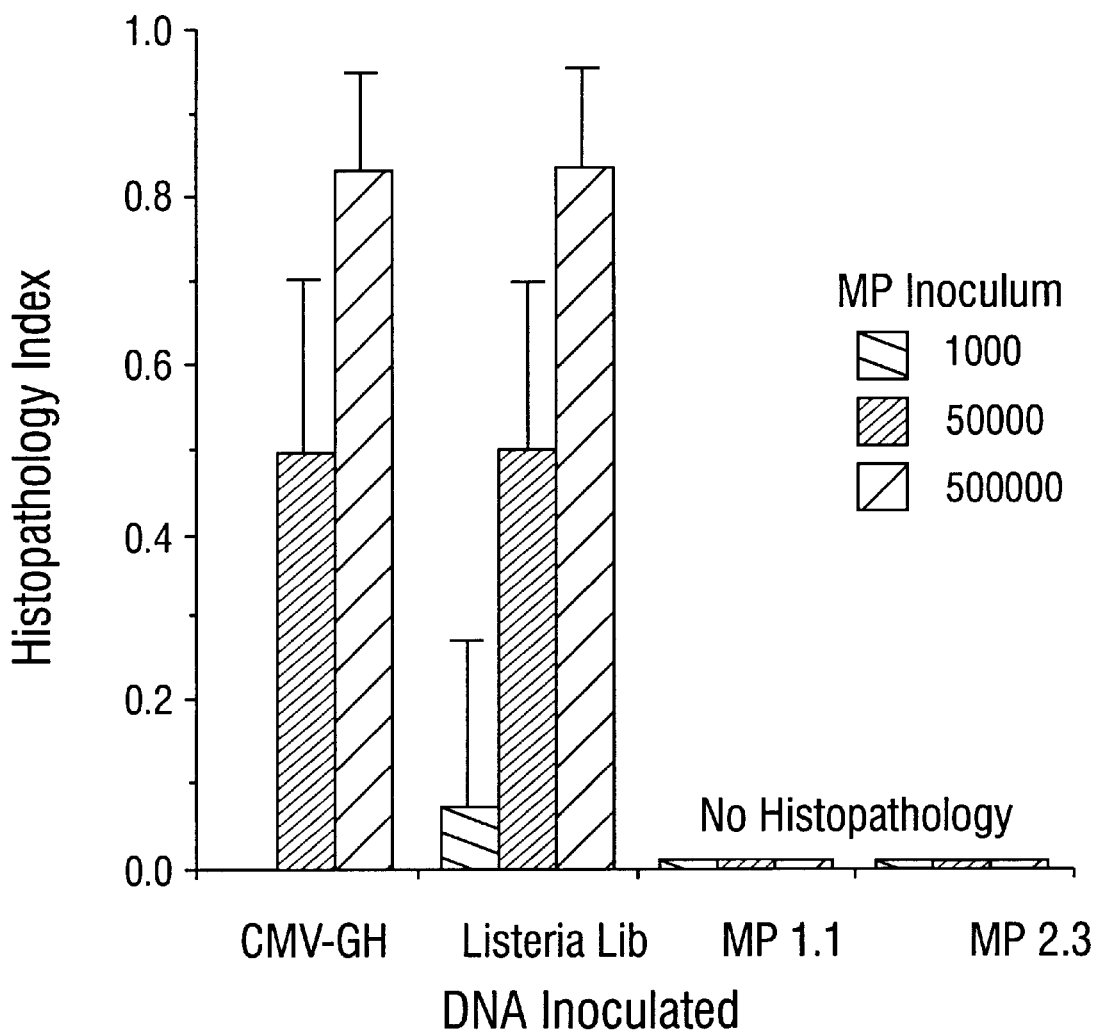
FIG. 4B. Histopathology of ELI immunized, MP-challenged mice. Lung sections from mice immunized with the indicated plasmids were stained and the degree of histopathologic lesions induced by MP infection was assessed and scored with a histopathology index. An index of 1.0 represents the maximal number of lesions observed in infected mice. An index of 0 indicates normal morphology. Each bar represents the mean from 2 to 4 mice. Error bars represent the standard deviation for each group.

Two of these sib libraries (MP1.1 and MP2.3) were inoculated separately into the skin of the ear of mice, with 10 mg introduced in a total of four inoculation sites. These inoculations contained ~1 mg of MP DNA, representing the equivalent of ~1×10$^9$ MP genomes—10$^6$-fold more than introduced in a normal MP infection. As negative controls, a plasmid encoding hGH alone or a comparable hGH fusion library with DNA from *Listeria monocytogenes* were inoculated in the same fashion. Sixty days after the first inoculation, and ten days after the last inoculation the mice were challenged by intranasal introduction of MP. Two weeks later, the mice were tested for MP infection. All of the control mice (non-inoculated and inoculated with hGH or Listeria DNA) had 10$^5$ to 10$^7$ mycoplasma in lung lavages even after the lowest (10$^3$) challenge. Lung sections from these mice showed significant lesions in the lung at the lowest challenge (FIGS. 4A and 4B).

Figure 5:
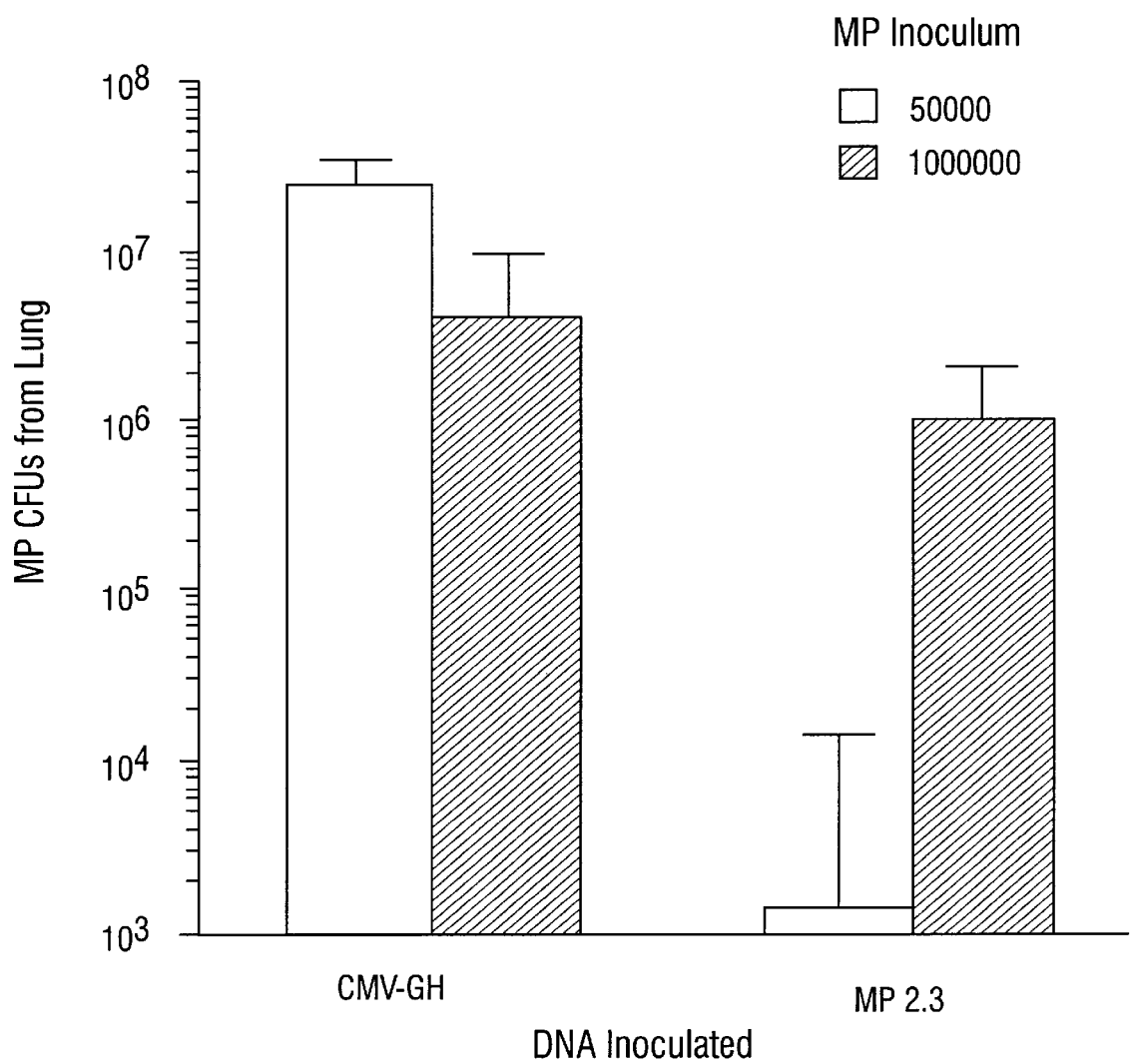
FIG. 5. MP titers from the lungs of mice 30 days after the start of immunization. 5–6 week old male Balb/C mice were immunized with 6 mg of CMV-GH-F2 or MP2.3 on day 1 and 3 mg on day 15, and 22. The mice were challenged with the indicated MP inoculum on day 30 and lung lavages were performed on day 44. MP CFUs from Lung represents the total number of MP from each group of mice as calculated from counting MP grown on plates from serial dilutions of lung lavages from the mice. Each bar represents the mean for 3 mice. Error bars represent the standard deviation for each group.

In remarkable contrast, the mice inoculated with either the MP1.1 or MP2.3 library had no culturable mycoplasma even at the highest challenge and showed no evidence of lung lesions (FIG. 5).

Figure 6:
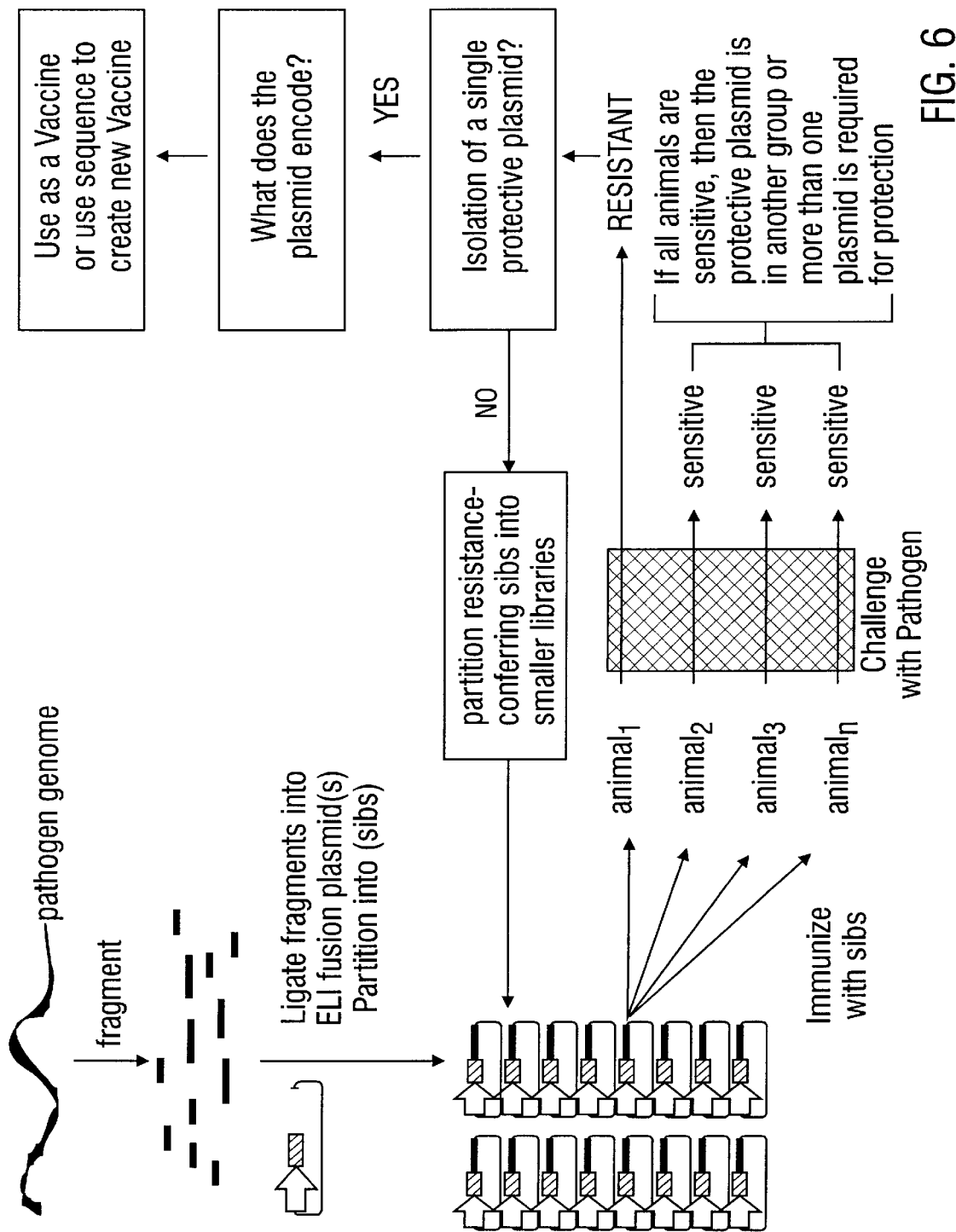
FIG. 6. Cartoon of generic ELI protocol for isolation of vaccine plasmids for any pathogen.

Anti-mycoplasma immune responses were characterized by several assays (Table 1). Mice vaccinated with libraries MP1.1 and MP2.3 demonstrated strong delayed-type hypersensitivity (DTH) to MP proteins, while there was little or no response in the control animals. Histological examination demonstrated massive mononuclear cell infiltration in the MP library-injected mice but not in control mice (data not shown). These DTH responses indicate that T-cells have been activated against mycoplasma antigens by inoculation of the MP libraries. Similarly, T-cells from mice immunized with MP1.1 or MP2.3 were primed to mycoplasma antigens and released migration inhibition factor (MIF) in macrophage migration inhibition tests. Mice were immunized as described in FIG. 6. Anti-hGH and anti-MP antibodies were measured by ELISA from sera taken 10 days after the second inoculation. 2 mice from each group were tested for DTH and MMI 12 days after the last immunization. Control refers to un-immunized mice. Results are shown in Table 1.

TABLE 1

Immune Responses Induced by ELI Libraries.

| | Anti-hGH Antibodies[1] | Anti-MP Antibodies[2] | MP-specific DTH (mm)[3] | MP-specific MMI (%)[4] |
|---|---|---|---|---|
| Control | − | − | 2.3 ± 0.4 | 0 |
| MP 1.1 | + | + | 16.4 ± 0.4 | 71.8 |
| MP 2.3 | + | + | 19.8 ± 0.3 | 73.3 |

[1]Antibody levels against hGH protein. (−) designates no antibodies, (+) indicates levels detectable only at dilutions of 1/250.
[2]Antibody levels against whole mycoplasma antigens. (−) designates no antibodies, (+) indicates levels detectable only at dilutions of 1/50.

TABLE 1-continued

Immune Responses Induced by ELI Libraries.

| Anti-hGH Antibodies[1] | Anti-MP Antibodies[2] | MP-specific DTH (mm)[3] | MP-specific MMI (%)[4] |
|---|---|---|---|

[3]MP-specific delayed-type hypersensitivity. Measurements indicate the change in footpad thickness induced by injection of MP antigens in PBS relative to that of PBS alone (20). Net footpad thickness (×100 mm) = [(post-MP injection minus pre-MP injection) minus post-PBS injection].
[4]MP-specific macrophage migration inhibition. Percent inhibition was calculated from the formula: (A − B)/A × 100, where A = the area of macrophage migration in media and B = the area of macrophage migration in media containing MP antigen (21).

Sera from MP1.1 and MP2.3 mice showed relatively low titers of antibodies against hGH and mycoplasma proteins (Table 1). Though all library members encode hGH and inoculation of hGH alone induced strong antibody titers, the fusion proteins may be restricted in their ability to be secreted and produce a humoral response. A similar low titer of hGH antibodies was observed with a Listeria library.

In another experiment, mice were immunized three times in a 30 day rather than 60 day regime to determine how rapidly protection could be initiated. This shortened protocol elicited substantial protection with the control mice having 10$^4$ more culturable pathogen at a given initial inoculum. However, unlike in the first experiment the protection was not as complete. This difference may arise because of the longer period of immune response before the challenge.

EXAMPLE 3

A Listeria ELI library was created in the same manner as that for mycoplasma.
Expression Library Immunization with Listeria.

Genomic DNA from *Listeria monocytogenes* was isolated and partially digested to an approximate mean fragment size of 0.4 kilobase pairs. These fragments were ligated into the human growth hormone sequence to generate a library which was sibbed into 21 sub-libraries of approximately 3000 transformants each. A larger set of sibs was constructed since the genome size of Listeria is approximately 4 times that of Mycoplasma.

A total of 10 mg of the indicated 3000 transformant sib(s) or parent plasmid was loaded on 0.5 mg of 1–3 mm gold microparticles and delivered into the ears of anesthetized 5–6 week old female Balb/C mice using a hand-held biolistic gene gun (Sanford et al. (1991)). The gene gun was used to maximize the efficiency of immunization. Mice were immunized 3 times over 60 days and challenged 7 days after final immunization with approximately 1×10$^5$ *Listeria monocytogenes* by intravenous injection into the tail vein. Three days later, the mice were sacrificed and listeria recovered from their spleens and counted.

Figure 7:
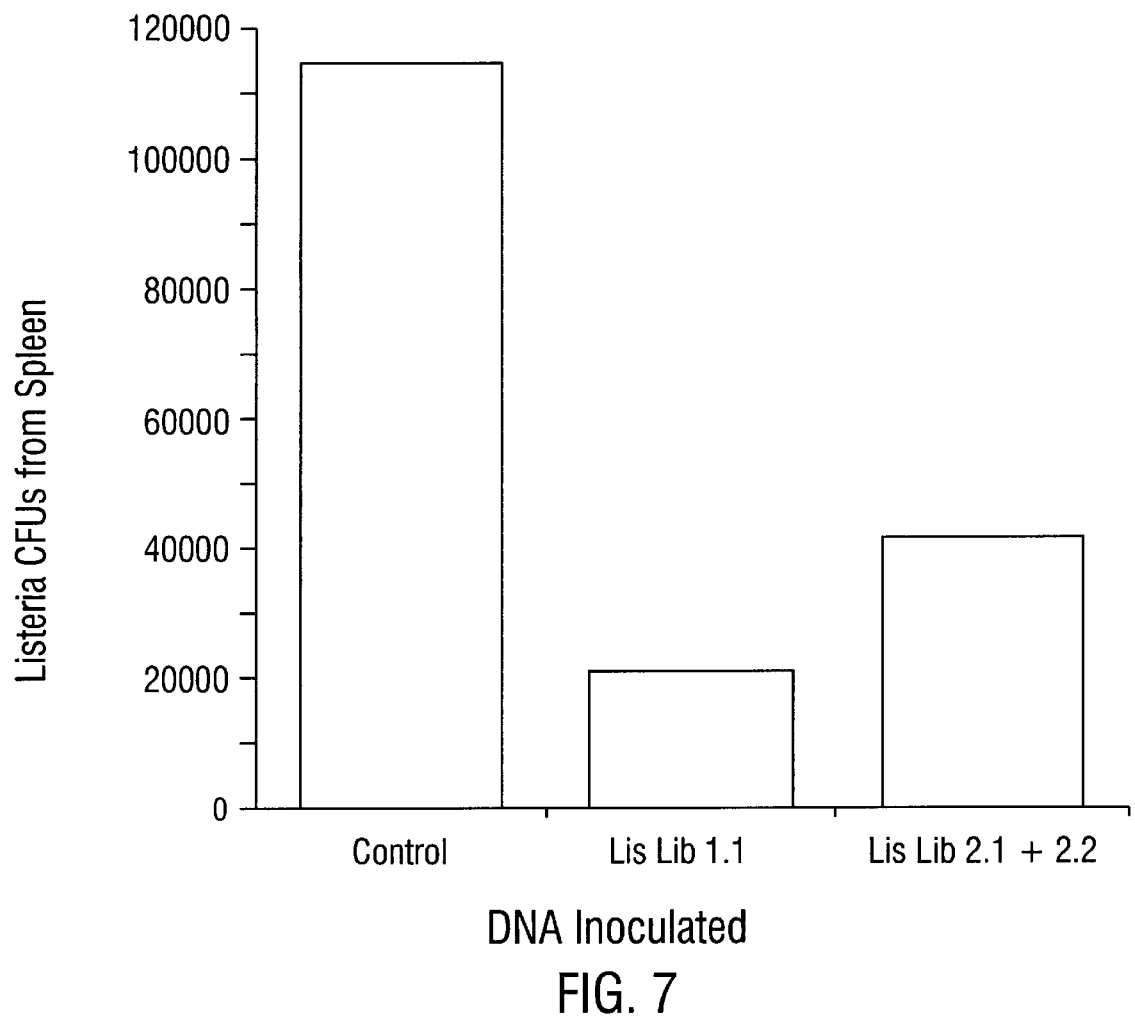
FIG. 7. Listeria monocytogenes titers from the spleens of ELI-immunized, Listeria monocytogenes-infected mice. 5–6 week old Balb/C female mice were immunized 3 times with 10 mg of Listeria library 1.1 or combined Lis lib 2.1+2.2. Lis Lib are libraries created by ligation of Listeria monocytogenes genomic MboI fragments cloned into CMV-GHF1&3 and CMV-GHF-2 as for MP. control (unimmunized) and EKI-immunized mice were challenged with $10^5$ listeria by i.v. injection and listeria CFUs were counted from spleen homogenates 3 days later.

Results are shown in FIG. 7. Inoculation with two of the sib libraries provided substantial protection on challenge with *Listeria monocytogenes* compared with controls.

EXAMPLE 4

The in vivo methods for identifying and developing expression library vaccines as described in Examples 2 and 3 are equally applicable to testing and sibbing of libraries ex vivo. This example illustrates an ex vivo method of identifying a vaccine.
Ex vivo Identification of Sib Library Vaccines Cells or sera from an animal immunized with a sib are tested for reaction against mammalian cells transfected with the same or another sib. To test for cellular responses, transfected cells are plated in 96 well plates a single or multiple clones per well. Cells from the blood, spleen, lymph nodes, or other sites are added to the wells and either CTL activity, proliferation, or cytokine secretion measured. A well in which a positive reaction occurs will indicate that the antigen gene transfected into the cell elicited the particular immune response which was assayed.

This approach allows particular modes of immune responses to be screened to avoid known deleterious immune events such as autoimmune damage in Chaga's disease (Parham, (1994). A similar approach is used with bacterial, viral, yeast, or other cellular carriers in the absence or presence of antigen presenting cells such as macrophages. Antibodies from sera or other sites could be tested against purified ELI antigens (e.g. glutathione fusions) or cellular extracts from the above carriers in an antibody capture ELISA. For those antigens that are secreted or located on the surface of the carrier, antibodies from the immunized mouse can capture these antigens in ELISA. Although most screening will preferably be performed using cells or antibodies from ELI-immunized animals, similar ex vivo screening may be performed using reagents from animals infected with the legitimate pathogen.

EXAMPLE 5

The inventors expect that MP genomic fragments may be cloned into the a fragment of b-galactosidase such that mycoplasma antigens will be synthesized inside the $E.$ $coli$. Engulfment of the bacteria will result in presentation of the mycoplasma antigen and immunization.

A similar library may be constructed where the mycoplasma antigens are secreted from the $E.$ $coli$ into the gut where they will activate IgA immunity which extends from the gastrointestinal tract into the lungs and nasal passages. These bacterial libraries will be introduced in other locations such as the peritoneum or sub-cutaneously to elicit immunity in other locations. The bacterial libraries can be introduced in osmotic pumps to avoid infection or as killed preparations.

An alternate bacterial host for the libraries is *Listeria monocytogenes*, since this bacterium invades macrophages and elicits MHC class I-restricted antigen presentation (Schafer, et al, 1992).

Antigen libraries can also be built onto the coat proteins of bacteriophages. For example, antigens can be added to the pIII and pVIII proteins of bacteriophage fdTET. An advantage of bacteriophage libraries is that they are expected to have no pathologic effect on the organism unlike living vectors.

Finally, ELI antigens can be created in vitro in $E.$ $coli$ expression systems by fusion to glutathione S-transferase or another fusion protein and inoculated into animals as a soluble protein bolus to elicit antibody responses.

Alternately, the library proteins can be introduced on agarose, paramagnetic, iron, or latex beads which can elicit cytotoxic T lymphocyte activity following phagocytosis of the beads by macrophages (Kovacsovics-Bankowski, et al, 1993).

EXAMPLE 6

In addition to inoculation of DNA into animals, it is expected that ELI can be performed using pathogen libraries transfected into syngeneic animal cells and the cells subsequently introduced into the animal. Once in the animal, the transfected cells can present library antigens to elicit immune responses. Library antigens may also be cloned into mammalian viruses such as adenovirus or vaccinia and inoculated into animals or cells rather than naked DNA.

Other approaches include expressing library antigens in $E.$ $coli$ or other bacteria (e.g. listeria), yeast, bacteriophages, or other cellular vehicles which can be introduced into the animal to elicit an immune response. Others have demonstrated that $E.$ $coli$ expressing a single mycoplasma antigen fused to b-galactosidase introduced into the gut of mice elicits immunity to mycoplasma (Lai, et al, 1994).

Figure 8:
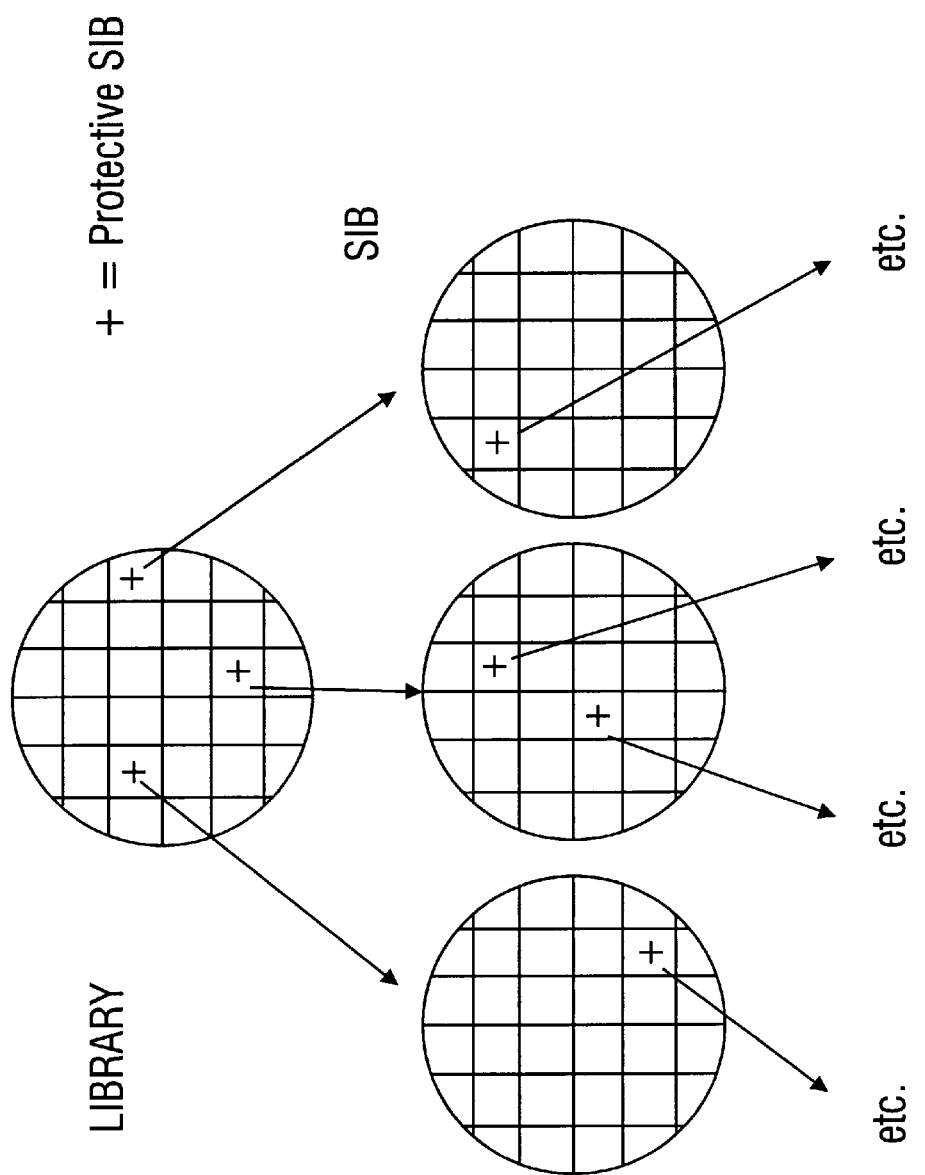
FIG. 8. Cartoon showing scheme for sibbing procedure for several independent protective plasmids.

A variety of approaches are contemplated for the isolation of individual vaccine genes using ELI. The success of each depends on the number and degree of cooperative effects between antigen genes. Two types of protective genes are expected to be detected in the practice of the disclosed method in the course of sibbing a library. As an example, a finite set of antigen gene fragments that are independently protective may be found for a particular pathogen. For these types of genes, a sequential sibbing protocol can be used in which a positive sib is divided into smaller sibs to be tested in the target organism for protection (FIG. 8). Reiterative sibbing and testing for protection will eventually isolate individual protective genes from the library. As the proportion of protective gene fragment increases in sequential sibs, protection should increase to some maximal amount. For example, in a 3000 transformant sib, only 3 ng of a single independent protective clone is delivered to an animal in 10 mg of sib DNA. After sibbing to a 100 transformant library now 100 ng of the positive clone would be delivered in a 10 mg immunization resulting in as much as a 33-fold increase in protection (up to a certain level). It is expected that these types of genes will have additive protective effects when combined with other genes of this class.

Figure 9:
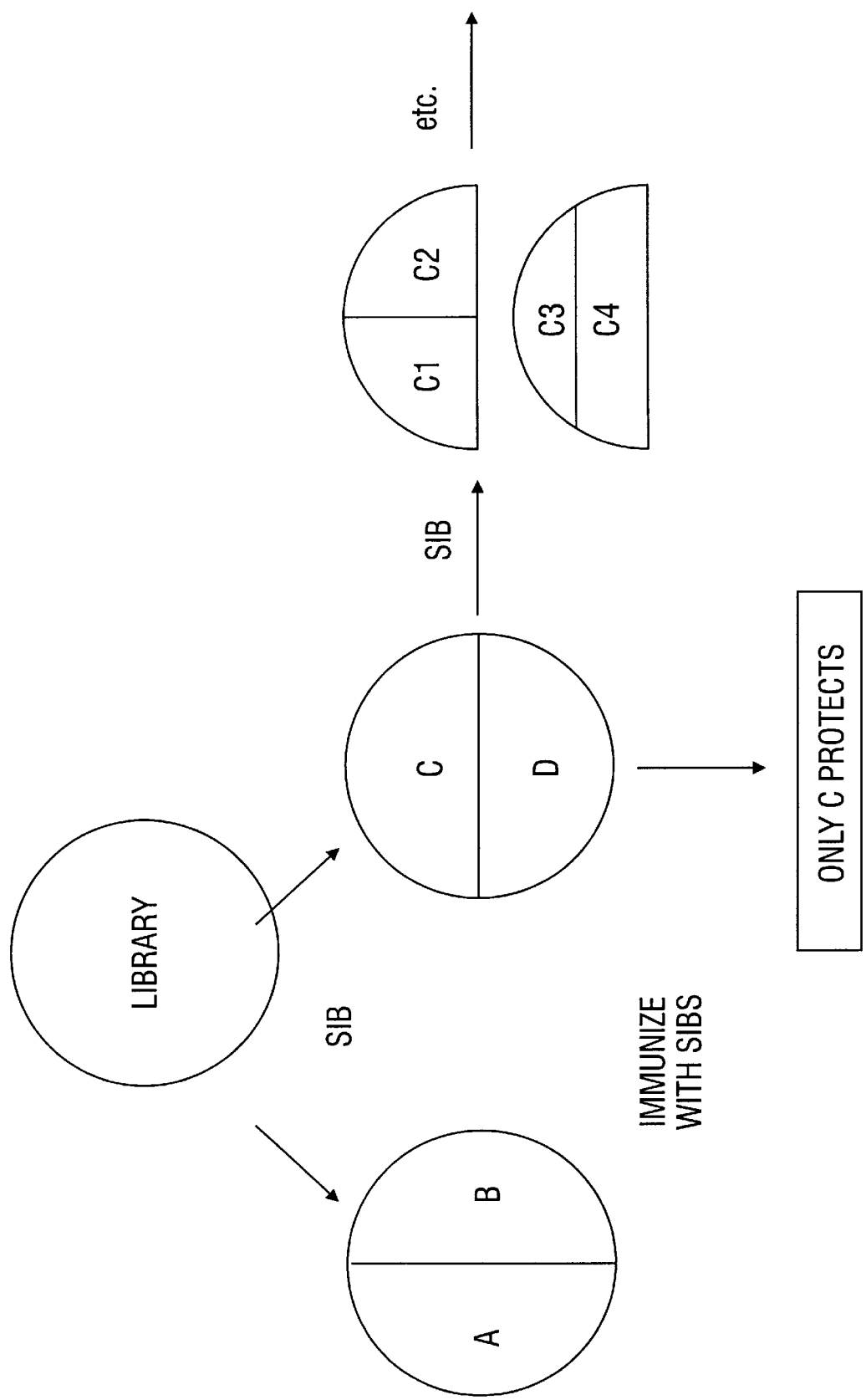
FIG. 9. Cartoon showing scheme for sibbing procedure to determine cooperative effects or additive threshold effects.
Figure 10:
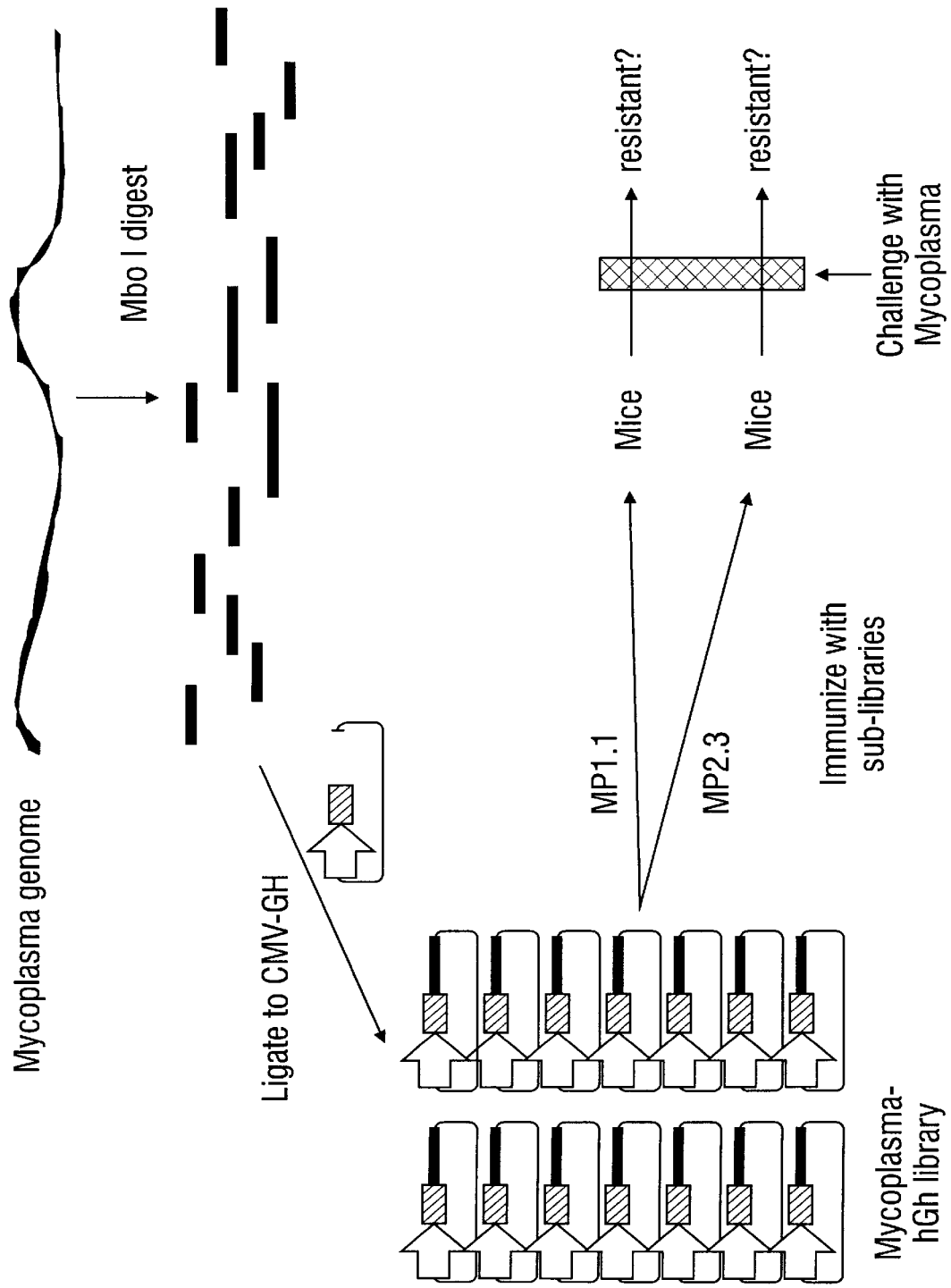
FIG. 10. Cartoon of the methodology of ELI against Mycoplasma pulmonis (MP). Libraries MP1.1 and MP2.3 consist of two different 3000 transformant sibs created by insertion of MP MboI fragments into frame 1 of CMV-GH-F1&3 and frame 2 of CMV-GH-F2, respectively. Balb/C mice were immunized as indicated using either MP1.1 or MP2.3 by gene gun delivery and the mice were subsequently challenged with MP and their resistance was assessed by titering MP from the lungs and by histochemical staining of lung sections as described in (Lai, et al, 1991). A set of mice with lower MP titers or histopathology indicated that one or more plasmids in the library confer resistance to MP by genetic immunization.

There may also be antigen genes that require the presence of one or more other antigen genes to confer resistance. In this situation, sequential sibbing will eventually result in near total loss of protection in all sibs at a certain level of division. To isolate these cooperative gene, a positive sib is divided into overlapping halves (FIG. 9) and tested in animals for protection. If only one half sib conferred resistance, this indicates that two or more cooperative genes are located in the two quarters and that loss of either totally abrogates protection. A positive half sib is then broken in alternate patterns to isolate a smaller sib containing the protective plasmids. This process is reiterated until the minimal set of genes is isolated.

Both approaches may be tested in parallel since both classes (and others) may be observed. Computer controlled sibbing is expected to facilitate this process since individual DNA isolates can be created at the beginning of the sibbing process and algorithms can be created to combine clones in either approach.

EXAMPLE 7

The expression library is constructed to represent at least a substantial portion of the pathogens genome. Bacterial pathogens have genomes of approximately $3\times10^6$ base pairs. If each fragment is about $1\times10^3$ bp, a genome equivalent would be approximately $1.8\times10^4$ clones considering only $\frac{1}{16}$ would be in frame. To capture all possible coding sequences, the fragments are ligated into vectors that place them into each of three forward coding frames, thereby generating a set of three master libraries. Three genome equivalents for each master library would be $5.4\times10^4$ clones. The master genomic expression library is maintained as a collection of sib libraries, each containing $\frac{1}{10}$ to $\frac{1}{20}$ of the total. The size of the sib library is dictated by certain considerations, including the lowest amount of DNA that can be inoculated and still produce an immune response.

Mycoplasm protection has been achieved with two different libraries of 3000 transformants (MP1.1 and MP2.3) containing an unknown number of protective antigen gene fragments. These sibs differ in that mycoplasma fragments were cloned into two different coding frames of human growth hormone. It thus appears unlikely that the same antigen fragment is conferring protection in both libraries, indicating that there are minimally 2 independent protective genes or an unknown number of cooperative protective genes in 6000 total transformants. Since only 1/6 of clones should express a real mycoplasma protein fragment, a minimal estimate is 1/500 expressing clones are protective. To estimate the maximal number of protective independent clones, 2 sibs were created from MP2.3 in which each contained 69 transformants (MP2.3.01 and MP2.3.02) and approximately 11 mycoplasma antigen-expressing clones each. Inoculation of these sibs into mice resulted in little or no protection. This suggests that the maximum number of independent protective clones is less than 1/22 expressing clones. From this it is estimated that there are approximately 10 to 200 independent protective antigen genes and an unknown number of cooperative genes in the total mycoplasma library of 27,000 transformants. A complete sibbed mycoplasma library sibbed to completion will allow an accurate estimate for this organism. FIG. 10 is a cartoon summarizing in general the immunization protocol.

For viral pathogens, sibbing will be proportionally simplified since their genomes are 10 to 1000-fold smaller than mycoplasma.

The results of the present work indicate that different organisms and different types of libraries (i.e. different fusion proteins, different delivery systems) will yield a wide numerical range of protective genes.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the methods described herein without departing from the concept, spirit and scope of the invention. More particularly, it will be apparent that the methods and concepts have a very wide range of application to virtually all categories of human and non-human pathogens and while demonstrated with two pathogens could be applied to any foreign DNA, including cancer. All such similar applications and substitutes apparent to those skilled in the art in view of the present disclosure and known techniques are deemed to be within the spirit, scope and concept of the invention as defined by the appended claims.

The following references as well as those cited in the specification are incorporated in pertinent part by reference herein for reasons cited in the text.

REFERENCES

Ada, G., *Mol. Immunol.* 28, 225 (1991).

Andersson, S., Davis, D. N., Déhlback, H., Jürnvall, H. and Russell, D. W. *J. Biol.Chem.* 264, 8222 (1989).

Ausubel, F. M. et al. Eds. *Short Protocols in Molecular Biology*, Greene Publishing Associates and John Wiley & Sons, New York, ed. 2, pp. 2–10 to 2–12 (1992).

Barry, M. A., Barry, M. E. and Johnston, S. A. *Biotechniques* 16, 616 (1994).

Campbell, "Monoclonal Antibody Technology, Laboratory Techniques in Biochernistry and Molecular Biology," Vol. 13, Burden and Von Knippenberg, Eds. pp. 75–83, Elsevier, Amsterdam, 1984.

Cassell, G. H. *Rev. Inf. Dis.* 4, 518 (1982).

Cohen, "Naked DNA Points Way to Vaccines," *Science,* 259:1691–1692, 1993.

Coney, L., Wang, B., Ugen, K. E., Boyer, J., McCallus, D. et al., *Vaccine* 12, 1545 (1994).

Conry, R. M., et al., *Cancer Res.* 54, 1164 (1994).

Cox, G. J. M., Zamb, T. J. and Babiuk, L. A. *J. Virol.* 67(9):5664–5667, 1993.

Davidson, M. K., Brown, M. B., Schoeb, T. R., Cassell, G. H. and Lindsey, J. R. *Rev. Infect. Dis.* 4, S243 (1982).

Davis, H. L., Michel, M. L., Whalen, R. G. *Hum. Mol. Gen.* 2, 1847 (1993).

Eisenbraun, M. D., Fuller, D. H., Haynes, J. R. *DNA Cell Biol.* 9, 791 (1993).

Fynan, E. F., Webster, R. G., Fuller, D. H., Haynes, J. R. and Santoro, J. C. et al., *Proc. Natl. Acad. Sci. USA* 90, 11478 (1993).

Gefter et al., *Somatic Cell Genet.* 3:231–236, 1977.

Goding, "Monoclonal Antibodies: Principles and Practice," pp. 60–74. 2nd Edition, Academic Press, Orlando, Fla., 1986.

Jameson & Wolf, *Compu. Appl. Biosci.,* 4(1):181–6, 1988.

Kohler and Milstein, *Eur. J Immunol* 6:511–519, 1976.

Kohler and Milstein, *Nature* 256:495–497, 1975.

Kovacsovics-Bankowski, M. et al. Efficient major histocompatibility complex class I presentation of exogenous antigen upon phagocytosis by macrophages. *Proc. Natl. Acad. Sci.* 90, 4942–4946 (1993).

Lai, W. C., Bennett, M., Lu, Y. S. and Pakes, S. P. *Infect. Immun.* 59,346 (1991).

Lai, W. C. et al., *J. Infect. Dis.* 161 1269 (1990). W. C. Lai and M. Bennett, in *Molecular and Diagnostic Procedures in Mycoplasmology*, S. Raziu and J. G. Tully, Eds. (Academic Press, Orlando, Fla., 1995 in press), Vol 1, Chap. 8.

Lai, W. C. et al. Protection of mice against experimental murine mycoplasmosis by a *Mycoplasma pulmonis* immunogen in lysogenized *Escherichia coli. Vaccine* 12, 291–298 (1994).

Lindsey, J. R., Cassell, G. H. and Baker, H. J. in *Pathology of laboratory animals*, K. Benirschke, F. M. Garner, T. C. Jones, Eds. (Springer Verlag Inc., New York, 1978), p. 1482.

Lowrie, D. B., Tascon, R. E., Colston, M. J. and Silva, C. L., Towards a DNA vaccine against tuberculosis. *Vaccine* 12, 1537–1540 (1994).

Maloy, S. R., "Experimental Techniques in Bacterial Genetics" Jones and Bartlett Publishers, Boston, Mass., 1990.

Maloy et al., "Microbial Genetics" 2nd Edition. Jones and Barlett Publishers, Boston, Mass., 1994.

Neimark, H. C. and Lange, C. S. *Nucleic Acids Res.* 18, S443 (1990).

Parham, P. Defence cuts begin to bite. *Nature* 356, 291–292 (1994).

Prokop, A., and Bajpai, R. K. "Recombinant DNA Technology I" *Ann. N.Y. Acad. Sci.* Vol. 646, 1991.

Rouse, B. T., Generic vaccines against herpes simplex virus. Gene therapy & nucleic acid vaccine strategies held Feb. 16–17, 1995, Bethesda, Md.

Sambrook, J. et al., "Molecular Cloning: A Laboratory Manual," Cold Spring Harbor Laboratory, Cold Spring Harbor, N.Y., 1989.

J. C. Sanford, et al. *Technique,* 3, 3 (1991).

Schafer, R. et al. Induction of a cellular immune response to a foreign antigen by a recombinant *Listeria monocytogenes* vaccine. *J. Immunol.* 149, 53–59 (1992).

Segal, I. H., "Biochemical Calculations" 2nd Edition. John Wiley & Sons, New York, 1976.

Tang, D., DeVit, M. and Johnston, S. A. *Nature*, 356:152–154, 1992.

Tayler, G. and Tayler-Robinson, D. *Immunology* 30, 611 (1976). G. Tayler and C. J. Howard, *Immunology* 43, 519 (1981).

Ulmer, J. B., Donnelly, J. J., Parker, S. E., Rhodes, G. H. and Felgner, P. L. "Heterologous Protection Against Influenza by Injection of DNA Encoding a Viral Protein," *Science*, 259:1745–1749, 1993.

Wang, B. et al., *Proc. Natl. Acad. Sci. USA*, 90:4156–4160, 1993.

Whitton et al., *J. Virol.* 67:(1)348–352,1993.

Wolf et al., *Compu. Appl. Biosci.*, 4(1):187–91 1988.

Xiang, Z. Q. et al., *Virology* 199, 132 (1994). A. Katsumi, N. Emi, A. Abe, Y. Hasegawa, Ito, M. et al., *Hum. Gene Ther.* 5, 1335 (1994).

Yamao, F., Muto, A., Kawauch, Y., Iwami, M. and Iwagami, S. et al., *Proc. Natl. Acad. Sci. USA* 82, 2306 (1985).

---

What is claimed is:

1. A composition comprising one or more antigens expressed from DNA segments obtained from a sib library of a cloned expression library prepared from a pathogen DNA or RNA wherein said one or more antigens produce a protective response to said pathogen in a vertebrate animal.

2. The composition of claim 1 which is comprised in a pharmaceutically acceptable vehicle.

3. The composition of claim 1 wherein the pathogen DNA is *Mycobacterium tuberculosis, Mycoplasma pulmonis,* Chlamydia or Listeria monocytogenes.

4. The composition of claim 1 wherein the vertebrate animal is a human.

5. The composition of claim 1 wherein the pathogen is HIV.

6. The composition of claim 1 wherein the pathogen is bacterial, viral, fungal or parasitic.

* * * * *